(12) United States Patent
Strakosas et al.

(10) Patent No.: US 12,061,163 B2
(45) Date of Patent: Aug. 13, 2024

(54) pH MODULATION DEVICE ARCHITECTURE MEDIATING METAL OXIDE CATALYSIS FOR METABOLITE SENSING

(71) Applicant: The Regents of the University of California, Oakland, CA (US)

(72) Inventors: Xenofon Strakosas, Santa Cruz, CA (US); John Selberg, Santa Cruz, CA (US); Marco Rolandi, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1036 days.

(21) Appl. No.: 16/968,441

(22) PCT Filed: Feb. 13, 2019

(86) PCT No.: PCT/US2019/017822
§ 371 (c)(1),
(2) Date: Aug. 7, 2020

(87) PCT Pub. No.: WO2019/160932
PCT Pub. Date: Aug. 22, 2019

(65) Prior Publication Data
US 2020/0400605 A1 Dec. 24, 2020

Related U.S. Application Data

(60) Provisional application No. 62/740,249, filed on Oct. 2, 2018, provisional application No. 62/629,959, filed on Feb. 13, 2018.

(51) Int. Cl.
*G01N 27/327* (2006.01)
*G01N 27/30* (2006.01)

(52) U.S. Cl.
CPC ....... *G01N 27/3275* (2013.01); *G01N 27/302* (2013.01)

(58) Field of Classification Search
CPC .................... G01N 27/302; G01N 27/3275
See application file for complete search history.

(56) References Cited

U.S. PATENT DOCUMENTS

| 10,313,290 B2 | 6/2019 | Chiu et al. |
| 2014/0061044 A1 | 3/2014 | Thekkedath et al. |

(Continued)

FOREIGN PATENT DOCUMENTS

| WO | 2012/018777 A1 | 2/2012 |
| WO | 2016/042343 A1 | 3/2016 |

OTHER PUBLICATIONS

C. f. D. C. a. Prevention, Atlanta, GA: Centers for Disease Control and Prevention, US Dept of Health and Human Services 2017.

(Continued)

*Primary Examiner* — Gurpreet Kaur
(74) *Attorney, Agent, or Firm* — Venable LLP; Henry J. Daley

(57) ABSTRACT

A non-enzymatic sensor includes a substrate; a sensor contact disposed on the substrate; and a pH modifying contact disposed on the substrate proximate the sensor contact. The pH modifying contact includes a material that absorbs hydrogen from and expels hydrogen to a fluid when in use in response to applied voltages resulting in an electrically controllable change of pH of the fluid. The pH modifying contact is positioned relative to the sensor contact such that the electrically controllable change of pH of the fluid results in a change in pH of the fluid proximal to the sensor contact to thereby enhanced detection of a substance of interest at the sensor contact without the use of enzymes.

20 Claims, 22 Drawing Sheets

(56) References Cited

U.S. PATENT DOCUMENTS

2016/0045144 A1     2/2016    Bansal et al.
2016/0235347 A1*    8/2016    Baig .................. A61B 5/14532

OTHER PUBLICATIONS

P. Zimmet, K. G. Alberti, D. J. Magliano, P. H. Bennett, Nat Rev Endocrinol 2016, 12, 616.
A. J. Bandodkar, J. Wang, Trends in Biotechnology 2014, 32, 363.
E. Witkowska Nery, M. Kundys, P. S. Jelen, M. Jonsson-Niedziolka, Anal Chem 2016, 88, 11271.
W. Gao, S. Emaminejad, H. Y. Y. Nyein, S. Challa, K. V. Chen, A. Peck, H. M. Fahad, H. Ota, H. Shiraki, D. Kiriya, D. H. Lien, G. A. Brooks, R. W. Davis, A. Javey, Nature 2016, 529, 509.
H. Yao, Y. Liao, A. R. Lingley, A. Afanasiev, I. Lähdesmäki, B. P. Otis, B. A. Parviz, Journal of Micromechanics and Microengineering 2012, 22, 075007.
A. J. Bandodkar, J. Wang, Trends Biotechnol 2014, 32, 363.
J. Kim, A. S. Campbell, J. Wang, Talanta 2018, 177, 163.
A. Martin, J. Kim, J. F. Kurniawan, J. R. Sempionatto, J. R. Moreto, G. D. Tang, A. S. Campbell, A. Shin, M. Y. Lee, X. F. Liu, J. Wang, Acs Sensors 2017, 2, 1860.
H. Lee, C. Song, Y. S. Hong, M. S. Kim, H. R. Cho, T. Kang, K. Shin, S. H. Choi, T. Hyeon, D.-H. Kim, Sci Adv 2017, 3.
Y.-T. Liao, H. Yao, A. Lingley, B. Parviz, B. P. Otis, IEEE Journal of Solid-State Circuits 2012, 47, 335.
B. J. van Enter, E. von Hauff, Chem Commun (Camb) 2018, 54, 5032.
H. Lee, Y. J. Hong, S. Baik, T. Hyeon, D. H. Kim, Adv Healthc Mater 2018, 7, e1701150.
C. De Block, B. Manuel-y-Keenoy, L. Van Gaal, J Diabetes Sci Technol 2008, 2, 718.
M. M. Rahman, A. J. Ahammad, J. H. Jin, S. J. Ahn, J. J. Lee, Sensors (Basel) 2010, 10, 4855.
K. Tian, M. Prestgard, A. Tiwari, Mater Sci Eng C Mater Biol Appl 2014, 41, 100.
K. E. Toghill, R. G. Compton, International Journal of Electrochemical Science 2010, 5, 1246.
X. Y. Lang, H. Y. Fu, C. Hou, G. F. Han, P. Yang, Y. B. Liu, Q. Jiang, Nat Commun 2013, 4, 2169.
Y. Ding, Y. Wang, L. Su, M. Bellagamba, H. Zhang, Y. Lei, Biosens Bioelectron 2010, 26, 542.
H. Zhu, L. Li, W. Zhou, Z. Shao, X. Chen, Journal of Materials Chemistry B 2016, 4, 7333.
S. R. Corrie, J. W. Coffey, J. Islam, K. A. Markey, M. A. Kendall, Analyst 2015, 140, 4350.
X. Strakosas, J. Selberg, Z. Hemmatian, M. Rolandi, Adv Sci 2017, 4.
C. Zhong, Y. Deng. A. F. Roudsari, A. Kapetanovic, M. P. Anantram, M. Rolandi, Nat Commun 2011, 2, 476.
E. E. Josberger, P. Hassanzadeh, Y. X. Deng, J. Sohn, M. J. Rego, C. T. Amemiya, M. Rolandi, Sci Adv 2016, 2.
Z. Hemmatian, S. Keene, E. Josberger, T. Miyake, C. Arboleda, J. Soto-Rodriguez, F. Baneyx, M. Rolandi, Nature Communications 2016, 7.
J. Soto-Rodriguez, Z. Hemmatian, E. E. Josberger, M. Rolandi, F. Baneyx, Advanced Materials 2016, 28, 6581.
T. Miyake, E. E. Josberger, S. Keene, Y. X. Deng, M. Rolandi, Apl Mater 2015, 3.
Y. X. Deng, T. Miyake, S. Keene, E. E. Josberger, M. Rolandi, Sci Rep-Uk 2016, 6.
Z. Hemmatian, E. Jalilian, S. Lee, X. Strakosas, A. Khademhosseini, A. Almutairi, S. R. Shin, M. Rolandi, Acs Appl Mater Inter 2018.
S. Park, H. Boo, T. D. Chung, Anal Chim Acta 2006, 556, 46.
P. Bollella, G. Fusco, C. Tortolini, G. Sanzo, G. Favero, L. Gorton, R. Antiochia, Biosens Bioelectron 2017, 89, 152.

* cited by examiner

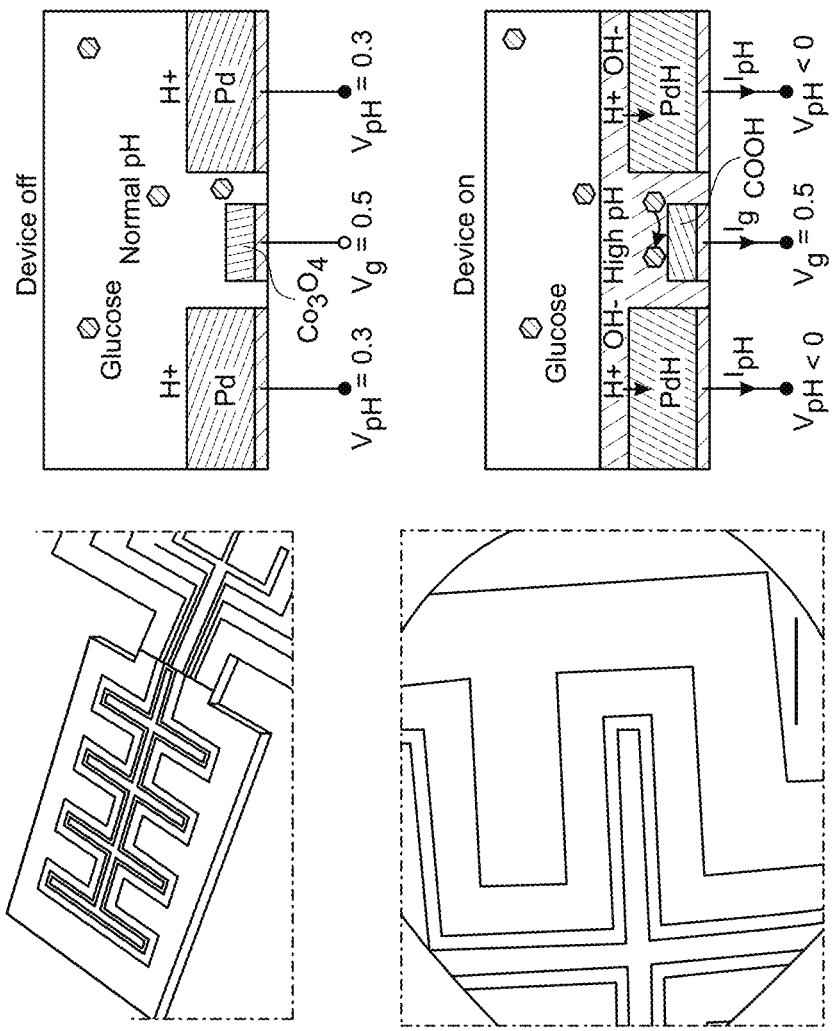
FIG. 7C
FIG. 7B
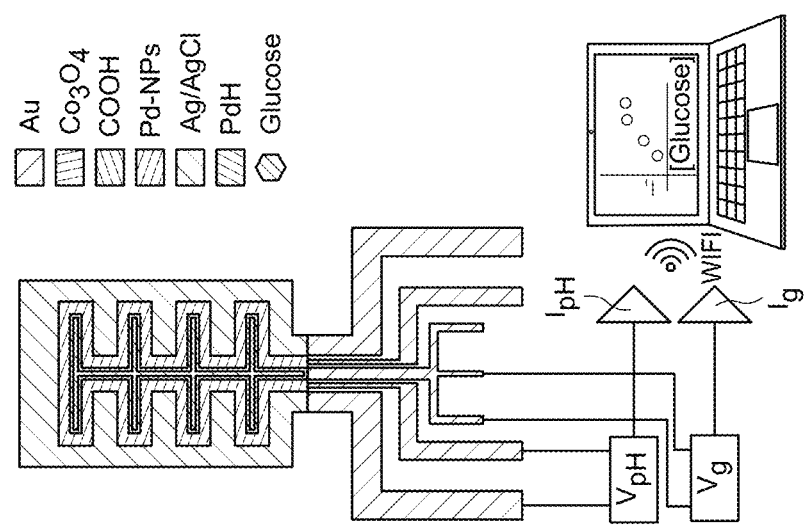
FIG. 7A pH MODULATION DEVICE ARCHITECTURE MEDIATING METAL OXIDE CATALYSIS FOR METABOLITE SENSING

CROSS-REFERENCE TO RELATED APPLICATIONS

This application is a U.S. National Stage Application under 35 U.S.C. 371 of PCT/US2019/017822, filed Feb. 13, 2019, which claims priority benefit to U.S. Provisional Patent Application No. 62/629,959, filed on Feb. 13, 2018 and to U.S. Provisional Patent Application No. 62/740,249, filed on Oct. 2, 2018, the entire content of each of which is incorporated herein by reference. All references cited anywhere in this specification, including the Background and Detailed Description sections, are incorporated by reference as if each had been individually incorporated.

BACKGROUND

1. Technical Field

The field of currently claimed embodiments of this invention relates to sensing devices, and more particularly to non-enzymatic sensing devices.

2. Discussion of Related Art

Continuous glucose monitoring from sweat and tears can improve the quality of life of diabetic patients and provide data for more accurate diagnosis and treatment. Current continuous glucose sensors use enzymes with approximately a one-to-two week lifespan, which forces periodic replacement. Metal oxide sensors are an alternative to enzymatic sensors with a longer lifetime. However, metal oxide sensors do not operate in sweat and tears because they only function at high pH (pH>10), and sweat and tears are neutral (pH=7).

Over 30.3 million people in the US have diabetes, a condition that now affects 18% of the worldwide population. Typically, a person with diabetes has to monitor their blood sugar level (2-20 mM range) up to five times a day to regulate their metabolism. This monitoring involves the "prick test" to extract the blood, which could be painful, especially for children. Patients that avoid or forget to monitor themselves could suffer health repercussions. In severe cases, these repercussions can be fatal. Continuous glucose monitoring (CGM) that uses minimally invasive sources such as sweat is less demanding for patients. It improves healthcare by provides a higher data collection rate with an increased reliability while avoiding the discomfort of the "prick test". The glucose concentration in sweat ranges from 0.2 mM to 0.6 mM, thus glucose sensing in sweat requires higher sensitivity than in blood. Devices capable CGM are particularly useful and many sensors exist that can detect glucose from sweat and tears. Google and Novartis have developed the smart Google contact lens, in which the sensing, storage, and transmission of the glucose levels occur on the contact lens. In a parallel path, glucose monitoring skin patches are able to measure glucose in sweat. All the above examples are enzymatic based sensors, the current standard for continuous monitoring of glucose. These sensors detect the presence of glucose by measuring the rate of glucose oxidation from the enzymes glucose oxidase or glucose dehydrogenase. For each glucose molecule oxidized, this reaction transfers an electron through a mediator to the sensing electrode. The sensing electrode records this electron transfer either by reading the electrode current or electrode potential. Enzymatic glucose sensors are highly sensitive, but the lifetime of these sensors is limited by decreasing enzymatic activity with time—typically one to two weeks. This relatively short lifetime increases costs and reduces scope.

Non-enzymatic glucose sensors based on metal oxides at the interface with nanostructured porous metals or carbon materials have longer lifetime because they do not contain a biological component. Metal oxide sensors detect glucose via the oxidation reaction of glucose with an activated metal oxide contact; the reaction results in an electron transfer to the contact which is recorded by the sensor as a current. A highly sensitive and stable substrate for glucose detection is cobalt oxide at the interface with nanoporous gold. However, this sensor only works in high pH (>11) because it requires the presence of hydroxide ions provided by a strong base such as 0.1-0.5M NaOH or KOH. This restriction of working only at high pH is not limited to cobalt oxide sensors but applies to many metal oxide and inorganic material-based sensors that oxidize target molecules. Thus, the development of metal oxide sensors for CGM applications has struggled since bodily fluids such as sweat and tears have a pH range of 4-7.

Therefore, there remains a need for improved sensing devices, such as improved non-enzymatic sensing devices that function in neutral fluids.

SUMMARY OF THE DISCLOSURE

An aspect of the present disclosure is to provide a non-enzymatic sensing device. The non-enzymatic sensing device includes a non-enzymatic sensor; and a power supply operatively connected to the non-enzymatic sensor. The sensing device further includes at least one of: i) a signal processing and display system in communication with the sensor system to received sensor signals therefrom to be processed and results displayed, or ii) a transmitter in communication with the sensor system to received sensor signals therefrom to be transmitted to an external device to be processed and results displayed. The non-enzymatic sensor includes: a substrate; a sensor contact disposed on the substrate; and a pH modifying contact disposed on the substrate proximate the sensor contact. The pH modifying contact includes a material that absorbs hydrogen ions from and expels hydrogen ions to a fluid when in use in response to applied voltages resulting in an electrically controllable change of pH of the fluid. The pH modifying contact is positioned relative to the sensor contact such that the electrically controllable change of pH of the fluid results in a change in pH of the fluid proximal to the sensor contact to thereby enhanced detection of a substance of interest at the sensor contact without the use of enzymes.

Another aspect of the present disclosure is to provide a non-enzymatic sensor including: a substrate; a sensor contact disposed on the substrate; and a pH modifying contact disposed on the substrate proximate the sensor contact. The pH modifying contact includes a material that absorbs hydrogen ions from and expels hydrogen ions to a fluid when in use in response to applied voltages resulting in an electrically controllable change of pH of the fluid. The pH modifying contact is positioned relative to the sensor contact such that the electrically controllable change of pH of the fluid results in a change in pH of the fluid proximal to the sensor contact to thereby enhanced detection of a substance of interest at the sensor contact without the use of enzymes.

Yet another aspect of the present invention is to provide a non-enzymatic method of detecting a substance of interest. The method includes disposing a fluid containing the substance of interest on a sensing contact; changing a pH of at least a portion of the fluid on the sensing contact by applying a voltage to a pH modifying contact that is also in contact with the fluid; and detecting the substance of interest using the sensing contact. The detecting is enhanced by the changing of the pH of the portion of the fluid on the sensing contact. The detecting is a non-enzymatic method of detecting.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

FIG. 7A depicts a schematic diagram of a non-enzymatic glucose biosensor, according to an embodiment of the present disclosure;

FIG. 7B is an optical image (top) of the modified contacts and a scanning electron microscope (SEM) image (bottom) of the platform, according to an embodiment of the present invention;

FIG. 7C is an electrical connection diagram depicting the operating principle for glucose sensor, according to an embodiment of the present invention;

DETAILED DESCRIPTION

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "substrate" is intended to have a broad meaning that can include a single layer of a material, multiple layers, laminated layers, composite layers, flexible structures, rigid structures, organic materials, inorganic materials, or combinations thereof. For example, and without limitation, substrates can be glass, plastic, or crystalline materials (e.g., silicon or another semiconductor).

The phrase "non-enzymatic sensing device" or "non-enzymatic sensor" refers to a device or sensor, respectively that does not require the use of an enzyme to perform the sensing or detection of the substance of interest. The term substance of interest can include, but is not limited to, glucose and nitric oxide.

Figure 1:
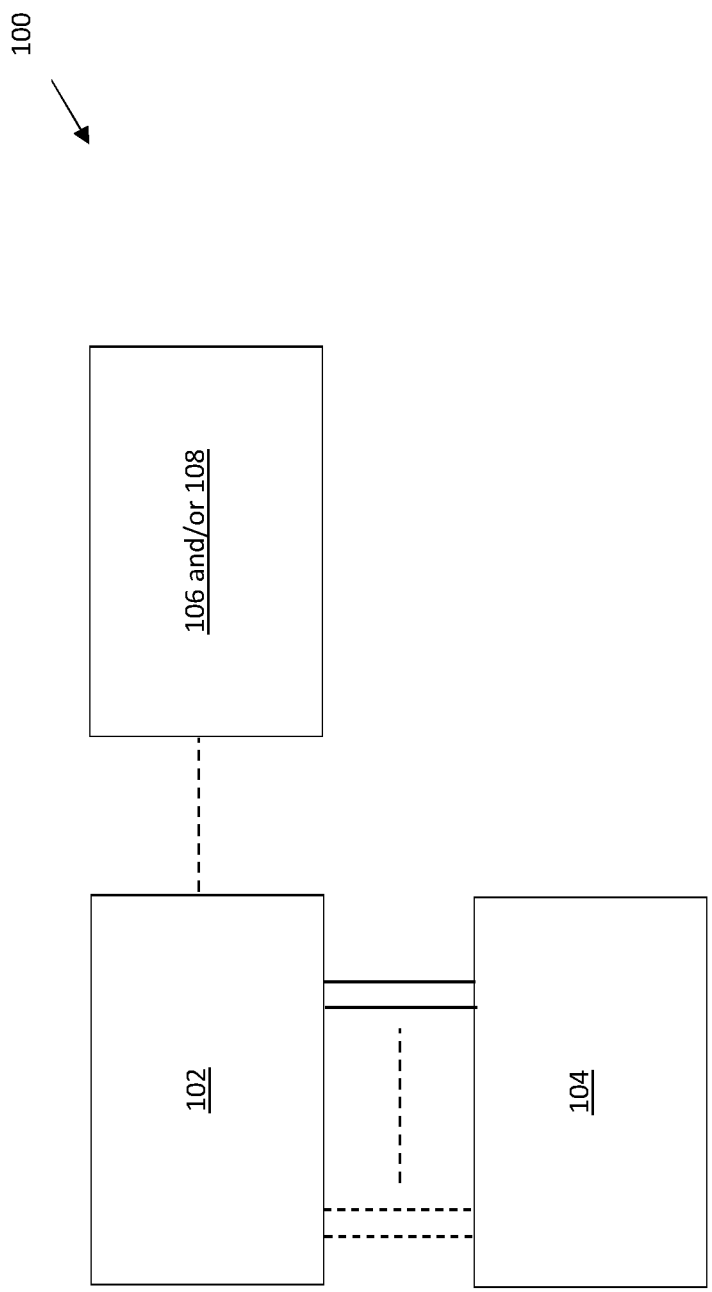
FIG. 1 is a schematic illustration of a non-enzymatic sensing device 100 according to an embodiment of the current invention.

FIG. 1 is a schematic illustration of a non-enzymatic sensing device 100 according to an embodiment of the current invention. The non-enzymatic sensing device 100 includes a non-enzymatic sensor 102, a power supply 104 operatively connected to the non-enzymatic sensor 102, and at least one of (1) a signal processing and display system 106 in communication with the sensor 102 to received sensor signals therefrom to be processed and results displayed, or (2) a transmitter 108 in communication with the sensor 102 to receive sensor signals therefrom to be transmitted to an external device to be processed and results displayed.

The power supply 104 can supply power to one or more circuits as is indicated schematically in FIG. 1. The power supply 104 can be, but is not limited to, one or more batteries, capacitors, super capacitors, or any combination thereof. The transmitter 108 in some embodiments of the current invention can transmit to a computer or smart phone (not shown) for example to be processed and further utilized in many possible ways.

In some embodiments, the sensor 102 can be on a flexible substrate such as, but not limited to polyethylene-terephthalate (PET) or Parylene-C and the glucose levels can be transmitted to a smartphone application or a smart watch, for example. However, the general concepts of the current invention are not limited to only these examples. In such an approach, two voltages can be applied and two currents read independently that will convert the signal to glucose concentration and pH, for example. The glucose data can be transmitted wirelessly via Bluetooth to a smart phone application, for example.

Figure 2:
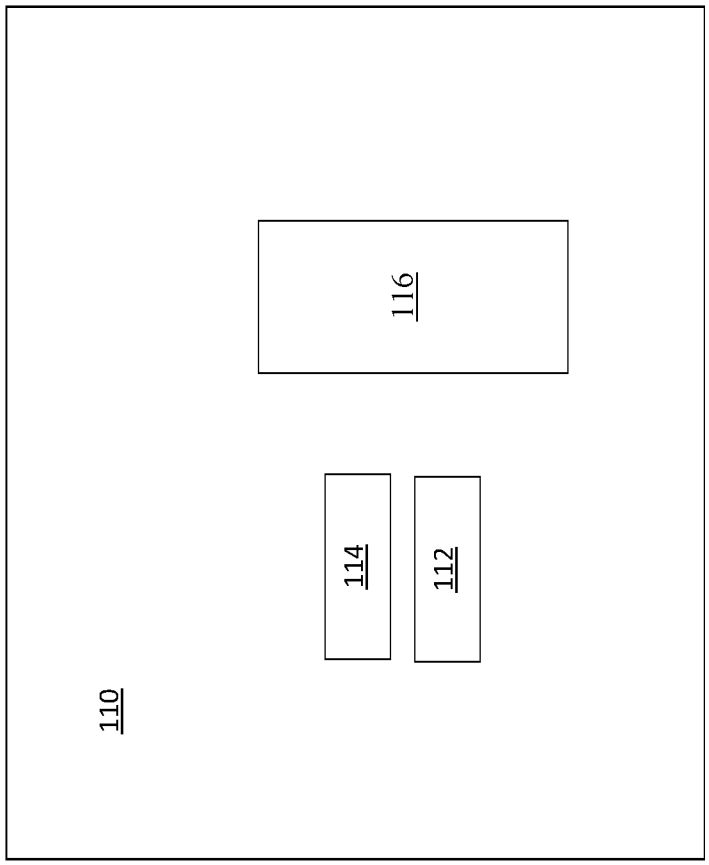
FIG. 2 is a schematic illustration of the non-enzymatic sensor 102 according to some embodiments of the current invention.

FIG. 2 is a schematic illustration of the non-enzymatic sensor 102 according to some embodiments of the current invention. The non-enzymatic sensor 102 includes a substrate 110, a sensor contact 112 disposed on the substrate 110, and a pH modifying contact 114 disposed on the substrate proximate the sensor contact 112. The electrical connections of sensor contact 112 and pH modifying contact 114 are not show in FIG. 2 for clarity, but can be seen in some of the embodiments described below.

The pH modifying contact 114 includes a material that absorbs hydrogen (e.g., hydrogen ions) from and expels hydrogen (e.g., hydrogen ions) to a fluid when in use in response to applied voltages resulting in an electrically controllable change of pH of the fluid. The pH modifying contact is positioned relative to the sensor contact such that the electrically controllable change of pH of the fluid results in a change in pH of the fluid proximal to the sensor contact to thereby enhanced detection of a substance of interest at the sensor contact without the use of enzymes. The term "hydrogen" is used herein to mean hydrogen ion, hydrogen atom or hydrogen molecule.

In some embodiments, the non-enzymatic sensor 102 can further include a reference contact 116 arranged to be in contact with the fluid so as to be isolated from or sufficiently far from the pH modifying contact so that a pH of the fluid proximate the reference contact remains substantially unchanged by the pH modifying contact during operation. The reference contact 116 can be disposed on the substrate 110 in some embodiments, or can be a separate component in other embodiments. In some embodiments, the reference contact 116 can include at least one of Ag, carbon nanotubes, carbon nanofibers, glassy carbon electrodes, or poly(3,4-ethylenedioxythiophene) polystyrene sulfonate (PEDOT:PSS). In some embodiments, the reference contact 116 can have a surface area greater than a surface area of the pH modifying contact 114 and greater than a surface area of the sensor contact 112.

In some embodiments, the non-enzymatic sensor 102 can further include a layer of the fluid disposed on the substrate.

In some embodiments, the pH modifying contact 114 can be in the form of at least a portion of an annular ring, and the sensor contact 112 can be arranged substantially at a center of the annular ring. In some embodiments, the pH modifying contact 114 can be thicker extending in a direction away from the substrate than a thickness of the sensor contact 112 so as to facilitate the change in pH of the fluid proximal to the sensor contact 112. In some embodiments, the pH modifying contact 114 can include at least one of Pd, polyaniline (PANI), a Pt/Pd alloy, a Pd/PANI alloys, or any combination thereof. In some embodiments, the pH modifying contact 114 can include Pd formed on a layer of gold. In some embodiments, the pH modifying contact 114 includes Pd nanoparticles having an ensemble average diameter of at least 60 nm and less than 1 μm. In some embodiments, the layer of gold is nanoporous in structure at least at an interface with the Pd. In some embodiments, the pH modifying contact 114 can further include a layer of Ti or Cr disposed on the substrate between the layer of gold and the substrate.

In some embodiments, the sensor contact 112 can include a catalyst for the detection of the substance of interest. In some embodiments, the catalyst can include a metal oxide. In some embodiments, the catalyst can include or be cobalt oxide and the substance of interest can be glucose. In some embodiments, the sensor contact 112 can further include a layer of gold between the substrate and the catalyst. In some embodiments, the layer of gold can be nanoporous in structure at least at an interface with the catalyst. In some embodiments, the sensor contact 112 can further include a layer of Ti or Cr disposed on the substrate between the layer of gold and the substrate.

In some embodiments, the substrate 110 can be a flexible substrate. In some embodiments, the substrate 110 can be a rigid substrate.

EXAMPLES

The following describes some embodiments in detail. The general concepts of the current invention are not limited to the specific embodiments described below.

Some embodiments of the current invention are directed to a device that electronically raises or lowers the pH of a solution around an electrode that contains the metal oxide catalyst, thereby catalyzing the reaction when a current flows through the electrode. When the catalysis is completed, the device restores the pH to the previous conditions.

Figure 3:
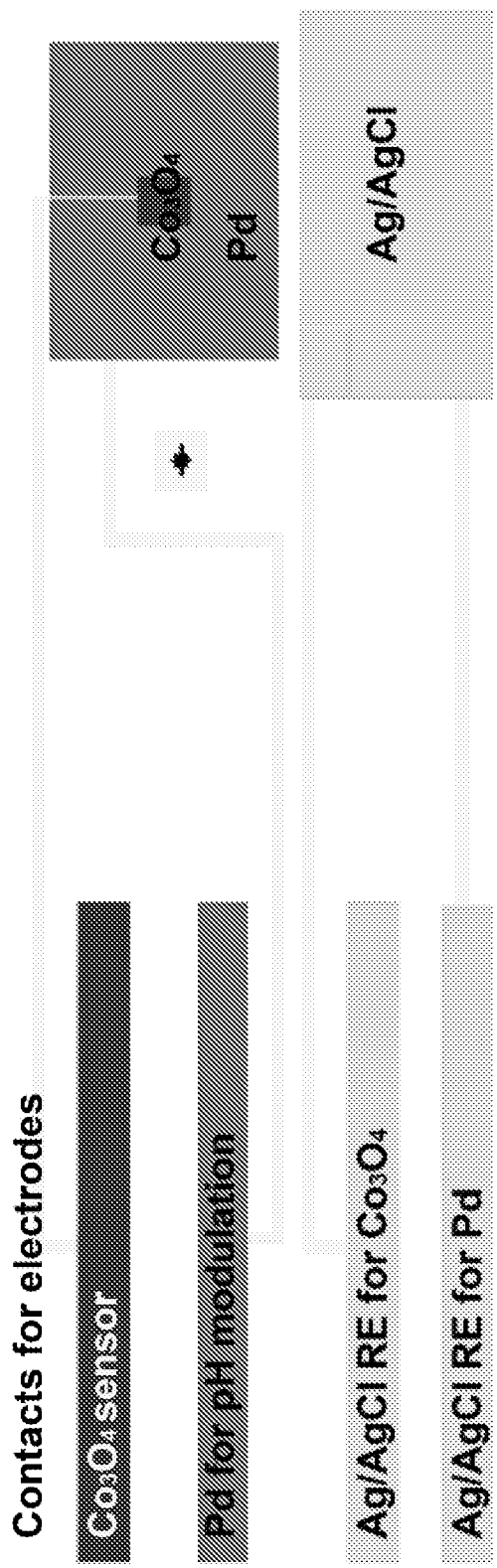
FIG. 3 is a schematic diagram of the device that electronically raises or lowers (modulates) the pH of a solution around an electrode that contains a metal oxide catalyst, according to an embodiment of the present invention.
Figure 5:
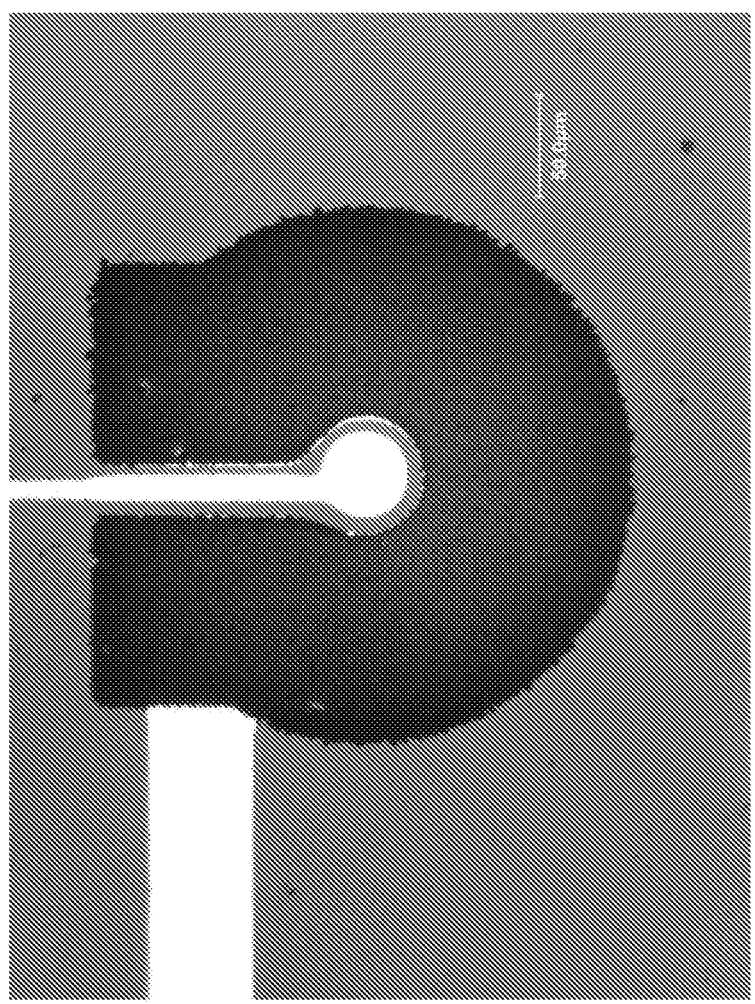
FIG. 5 is a photograph of a device active area described where the dark region corresponds to the Pd nanoparticles deposited on gold, according to an embodiment of the present invention.

FIG. 3 is a schematic diagram of the device that electronically raises or lowers (modulates) the pH of a solution around an electrode that contains a metal oxide catalyst, according to an embodiment of the present invention. An embodiment of the current invention is directed to a non-enzymatic glucose sensor that includes a palladium platform (a substrate of metal Au with palladium nanoparticles electrodeposited on the surface of the Au) surrounding a surface functionalized with a metal oxide, such as cobalt oxide. Cobalt oxide catalyzes the oxidation of glucose at a pH of about 13-14, while biological samples are generally at a pH of about 7-8. FIG. 5 is a photograph of a device active area described where the dark region corresponds to the Pd nanoparticles deposited on gold. The circle in the center region is cobalt oxide deposited on gold.

Figures 4A, 4B:
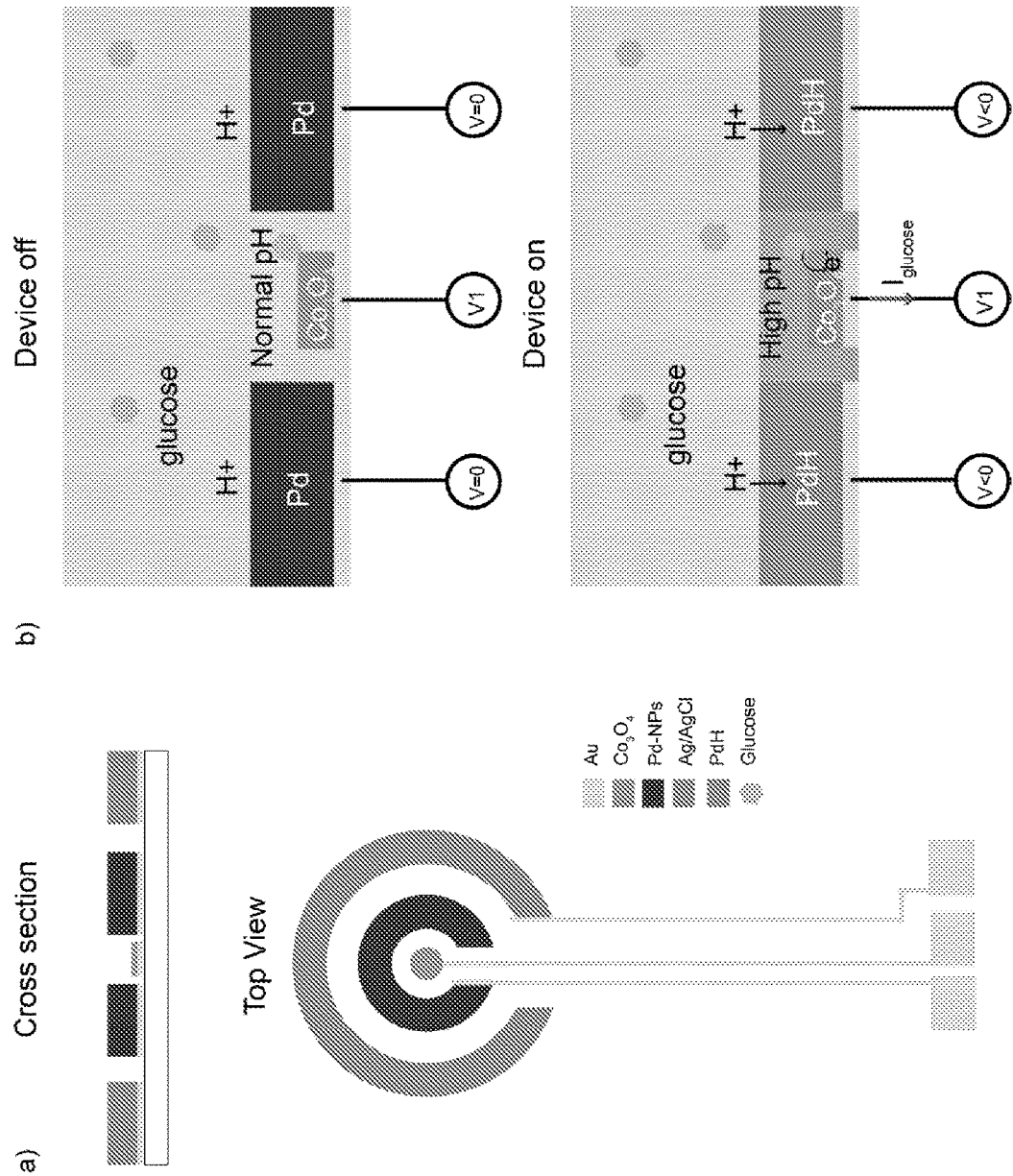
FIG. 4A is a cross-section and a top view of the various electrodes in the device, according to an embodiment of the present invention.
FIGS. 4B and 4C are schematic electrical diagrams of the device illustrating the operation of the device in an OFF state and an ON state, according to embodiments of the present invention.

FIG. 4A is a cross-section and a top view of the various electrodes in the device according to an embodiment of the present invention. In an embodiment, the black semi-ring corresponds to Pd-NPs and the gray semi-ring corresponds Ag/AgCl, and the dot or disk in the middle corresponds to $Co_3O_4$. In an embodiment, gold electrical lines are used for electrical voltage supply to the various materials, as shown in FIG. 4A.

Figure 4C:
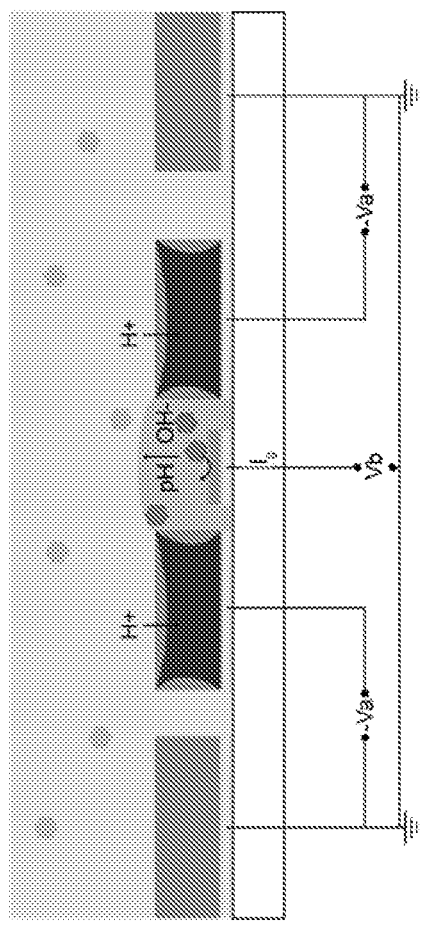
Figure 4C:
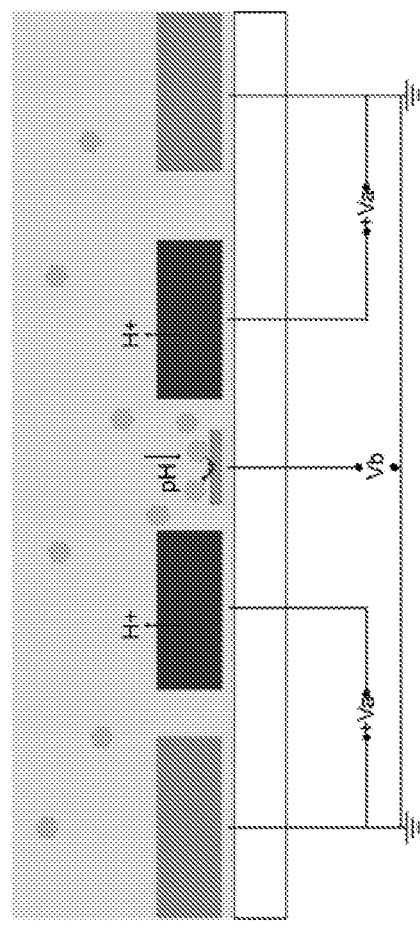
Figure 4D:
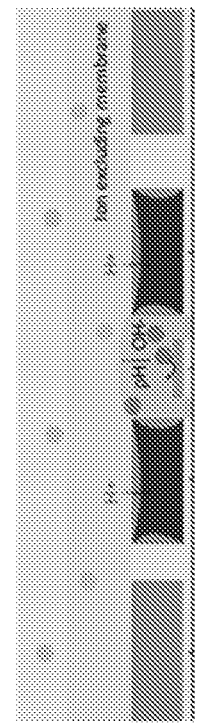
FIG. 4D is a cross sectional view of the device similar to FIGS. 4B and 4C but with an ion excluding membrane separating the alkaline pH in the device active area from a biological environment, according to an embodiment of the present invention.

FIGS. 4B and 4C are schematic electrical diagrams of the device illustrating the operation of the device in an OFF state and an ON state, according to embodiments of the present invention. FIG. 4D is a cross sectional view of the device similar to FIGS. 4B and 4C but with an ion excluding membrane separating the alkaline pH in the device active area from a biological environment, according to an embodiment of the present invention. Similar electrical connections can be used in the embodiment shown in FIG. 4D in a similar fashion as shown in FIGS. 4B and 4C. When the device is ON, the Pd makes the environment around the cobalt oxide basic, which activates glucose oxidation. When the device OFF, PdHx releases protons back into the environment neutralizing the solution pH. In an embodiment, an electrical potential of V=−0.9 to −1.5 V, applied to the palladium contact, drives protons into the palladium, resulting in palladium hydride formation which in turn results in the solution near the contact becoming more alkaline, as shown in FIG. 4B. The change towards alkaline pH results in a gradient in pH radiating out from the Pd contact, with the pH being highest at the Pd-solution interface. The higher pH activates the cobalt oxide such that it can sense glucose in solution when an appropriate potential vs a reference contact is held. After the measurement of glucose, a positive potential is applied to the palladium hydride that induces the release of protons into solution. This returns the solution to the original pH and reforms the palladium.

Effective Voltage Range for Sensing Glucose on CoOx:

There is an effective range of sensing, from V=0 V to V=0.6 V Vs Ag/AgCl. And this can be shown from a cyclic voltammetry. It is also shown that the lower the applied voltage the better the selectivity towards glucose. In blood, Uric Acid and Ascorbic Acid can be oxidized by the $Co_3O_4$ sensor at positive potentials. So, the smaller the potential of the sensor the lower the interference.

Inventors' observations show that palladium hydride will release protons at 0V. We sometimes use a small positive potential (in the range of +0.1-0.2V) to make this happen faster. However, we believe 0V is sufficient for this device. So, there is no need of positive potential in the Pd electrode.

Device Geometry:

The concentric geometry between Pd and the metal-oxide contacts can be important in some embodiments of the current invention. Ideally, the pH change induced by the Pd electrode will diffuse uniformly over the entire metal-oxide contact; a concentric geometry makes this more likely. Also, there is a much larger number of Pd nanoparticles deposited on the Pd contact than cobalt particles on the metal-oxide contact thereby forming a "wall" around the more planar contact which in turn makes the pH change near the cobalt contact.

The silver chloride reference electrode need not be arranged in a concentric pattern—although this is shown in FIGS. 4A, 4B, 4C, 4D, and 5, a concentric pattern is not required and non-concentrically arranged reference electrodes have also been used. The reference electrode(s) can be separate from the substrate. For example, Ag/AgCl wire electrodes were connected to a transmitter while the Pd and metal oxide layers were on glass. In further embodiments, two AgCl reference contacts can be used—one electrode for each of the Pd and metal-oxide contacts.

In some embodiments, the distance between the Pd and metal-oxide contacts is 40 µm or less. Shorter distances result in a faster change of the pH at the metal-oxide surface, which in turn can improve sensing.

The geometry and distance between the reference electrodes and the Pd and metal-oxide contacts can be any distance that is sufficiently large to provide the compensating half reaction. One of skill in the art in light of this disclosure can determine such a distance without undue experimentation.

The following is one example for how the device can be fabricated. One of skill in the art in light of this disclosure can appreciate that other fabrication methods can be used.

Device Fabrication:

A 5 nm Cr adhesion layer and a 100 nm thick Au layer were evaporated on glass microscope slides. For each of the following steps a photoresist S1813 defined the active area and protected the rest of the metal from contamination. At the end of each process the photoresist was removed with acetone, isopropanol, Di water, and N2 respectively.

Nanoporous Au:

Nanoporous Au electrodes were produced by electrochemically etching the Au layer with 1.5M $ZnCl_2$ at a temperature between 95° C. and 125° C. A single-cycle cyclic voltammetry routine from 0.5V to −1.4V vs AgCl (for example starting at −0.9V and stopping at 0.4V) was performed with a Metrohn Autolab Potentiostat (PGSTAT128N). This routine corresponds to two rounds of Zn—Au alloying/dealloying.

It is noted that Ag/AgCl is used as the reference electrode in this process. The potentials used are relative to the standard potential of an Ag/AgCl electrode and will change if a different reference electrode is used. For example, this method could use a reference electrode made from zinc wire.

The two rounds of Zn—Au alloying/dealloying correspond to: (1) the starting point of the current voltage CV which is at −0.9V where the $Zn^{2+}$ ions will be binding the Au contact. As the voltage increases towards +0.5V the $Zn^{2+}$ will start to enter the solution pulling away gold. The switch from alloying to dealloying of $Zn^{2+}$ happens around −0.4V. Additional CV ensures that all the $Zn^{2+}$ is removed from the surface of the electrodes; (2) The second round of CV is a sweep down to −1.4V which results in a greater amount of $Zn^{2+}$ binding to the surface than the previous round. Again, as the voltage sweeps positive to 0.5V, the $Zn^{2+}$ is stripped from the contact, also removing Au.

Cobalt Deposition:

Electrochemical: Deposition of cobalt oxide on Au was performed using a three-electrode electrochemical cell equipped with a Pd counter and AgCl glass reference electrodes. Cobalt Oxide nanoparticles were deposited from a solution of 5 mM Cobalt (II) Sulfate suspended in 0.1M $H_2SO_4$ at −0.8V vs AgCl. This was performed with a Metrohn Autolab Potentiostat (PGSTAT128N).

Hydrothermal:

Porous Au electrodes were transferred into a Teflon-lined stainless steel autoclave filled with a mixture of 6 mM $Co(SO_4)$ in a 10 ml deionized-water and 60 ml of 100% ethanol. The incubator was placed in an oven of 180° C. for 5 min. After reaching room temperature, the samples were rinsed with deionized water.

Pd Deposition:

Deposition of Pd NPs on Au was performed using a three-electrode electrochemical cell setup with a Pt counter and AgCl reference electrodes. Pd NPs were deposited from a 1% solution of Palladium (II) Nitrate at −0.4V.

Silver Deposition:

Deposition of Ag on Au was performed using a mix of silver nitrate 0.1 M and Iron (II) Chloride 0.1 M on top of the active Au contact. It is noted that other materials can serve the same purpose as the silver here and those can include, but are not limited to, carbon nanofiber, glassy carbon electrodes decorated with carbon nanotubes, and PEDOT:PSS.

How the Device is Used:

The platform can be fabricated on top of a flexible substrate such as Parylene-C, PET, or Polyimide or on a rigid surface like glass or silicon wafers, for example.

Figure 6:
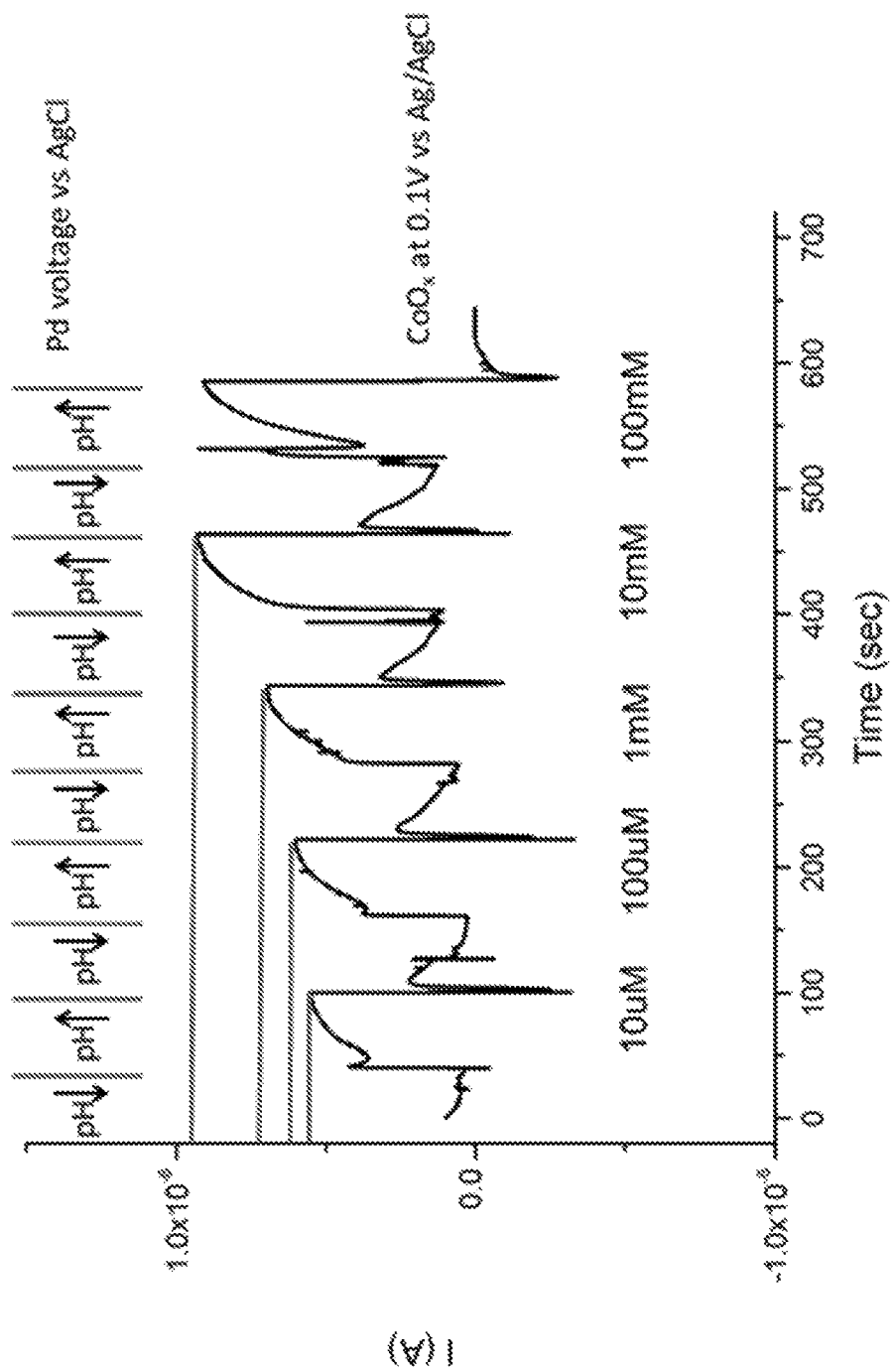
FIG. 6 is a plot of the output current recorded at the CoOx contact over time as the pH is increased using the Pd contact in the presence of the indicated concentration of glucose in a 0.1 M NaCl solution during device ON/OFF cycles which pH modulated by Pd contacts, according to an embodiment of the present invention.

FIG. 6 is a plot of the output current recorded at the CoOx contact over time as the pH is increased using the Pd contact in the presence of the indicated concentration of glucose in a 0.1 M NaCl solution during device ON/OFF cycles which pH modulated by Pd contacts, according to an embodiment of the present invention. A V=0.2 V vs Ag/AgCl was constantly applied at the CoOx electrode. At physiological pH the recorded current was in the order of pA. Then a V=−1 V vs a different Ag/AgCl electrode modulates the pH. While the pH is increasing, the current recorded at the CoOx electrode is an order of magnitude higher. Higher current also correlates with higher glucose concentration.

FIG. 7A depicts a schematic diagram of a non-enzymatic glucose biosensor, according to an embodiment of the present disclosure. As shown in FIG. 7A, A Pd contact (outside thick line) locally creates basic conditions by absorbing H+ into its lattice when VpH is negative. In basic conditions, a nanoporous $Au/Co_3O_4$ (inside line) contact catalyzes glucose to gluconic acid when VG is positive. Two Ag/AgCl electrodes (grey) act as reference electrodes to the Pd and $Au/Co_3O_4$. A small conditioning board controls the device, acquires current, and transmits wirelessly to an external device.

FIG. 7B is an optical image (top) of the modified contacts and an SEM image (bottom) of the platform, according to an embodiment of the present invention. Gold (Au) contacts were modified with Pd, nanoporous Au coated with $Co_3O_4$, and Ag/AgCl by using electrodeposition. The SEM image (bottom) of the platform shows the interdigitated contacts with a 20 gm gap between each contact. The scale bar is 1 mm.

FIG. 7C an electrical connection diagram depicting the operating principle for glucose sensor, according to an embodiment of the present invention. When the device is OFF (top), VpH=0, the pH is at physiological values—typically pH=7. Even with Vg=0.5 V, the $Au/Co_3O_4$ does not oxidize glucose and Ig=0. When the device is ON (bottom), VpH=−1V, the Pd contact absorbs $H^+$, removes $H^+$ from the solution and thus increases its pH. At high pH, the $Au/Co_3O_4$ contact is its more reactive $CoO_2$ oxidized state. With Vg=0.5 V, the $CoO_2$ contact oxidizes the glucose molecule and the resulting electron is collected by the contact as Ig, which increases with glucose concentration.

In an embodiment, the glucose sensor includes the bioelectronic control of pH in the proximity of the cobalt-oxide sensor surface enabling sensing glucose at high pH even in an otherwise neutral fluid. The glucose sensor comprises cobalt oxide ($Co_3O_4$), palladium (Pd), and silver/silver chloride (Ag/AgCl) contacts grown on gold (Au) strips defined on a glass substrate. The $Co_3O_4$ contact is the sensing element, the Pd contact is used to change the local pH of the fluid, and the Ag/AgCl contacts act as reference electrode, as illustrated in FIGS. 7A and 7B. These contacts are connected to an external circuit board that provides control voltages ($V_g$ for the $Co_3O_4$ and $V_{pH}$ for Pd), measures the contact current (Ig for $Co_3O_4$ and IpH for Pd), and provides signal analysis and wireless communication to a personal computer, as shown in FIG. 7A. The novelty of this glucose sensor is the ability to create localized and transient alkalosis for glucose sensing to occur on the cobalt oxide contact even in neutral fluids, as illustrated in FIG. 7C. The transient alkalosis may be needed because in neutral pH, at low voltage (e.g., $V_g$ equal about 0.5V), the glucose oxidation reaction does not occur on the $Co_3O_4$ contact and thus the presence of glucose cannot be detected. In order to induce local alkalosis, we set $V_{pH}$ at about −1 V, which removes $H^+$ from the solution by first reducing $H^+$ into H at the Pd/solution interface and then absorbing H into the Pd metal to form $PdH_x$ with x<0.6. In this way, the inventors have demonstrated transfer of $H^+$ to and from hydrated proton conducting polymers and membrane proteins, and modulation of solution pH for monitoring enzymatic reactions controlling bioluminescence, and targeted cargo delivery to cells. Setting the value of $V_{pH}$, the pH of the fluid can be controlled by multiple units in proximity to the cobalt oxide contact, thus creating a local environment to for glucose sensing to occur.

Figure 8A:
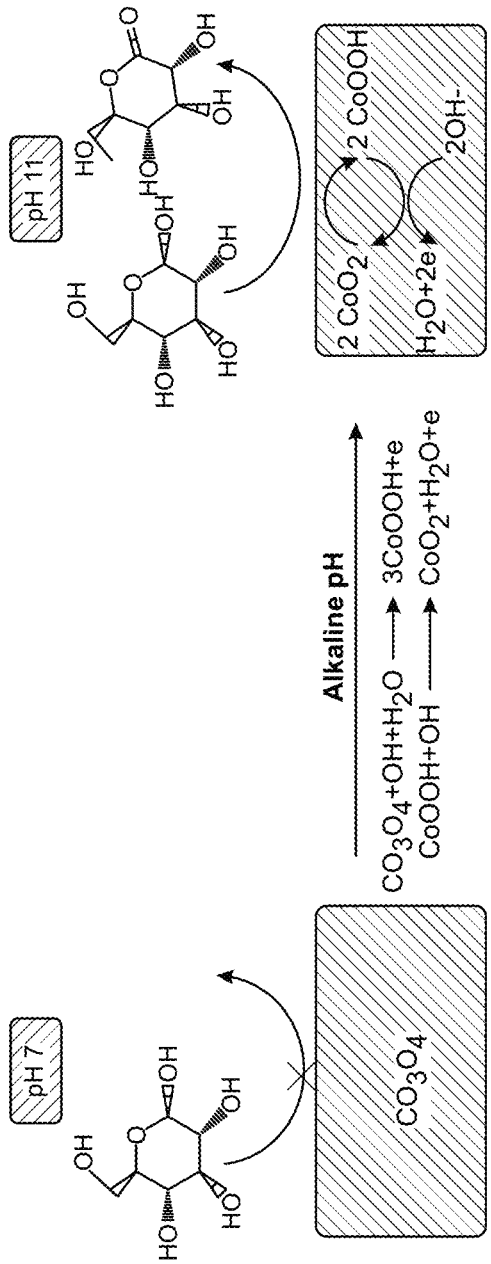
FIG. 8A is a schematic diagram depicting a sensing mechanism of cobalt oxide contacts, according to an embodiment of the present invention.
Figure 8C:
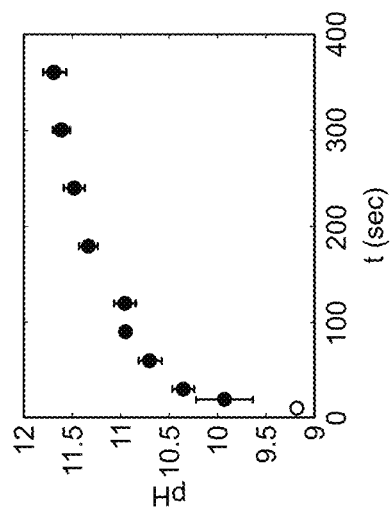
FIG. 8C is a plot of pH measurements versus time, according to an embodiment of the present invention.
Figure 8B:
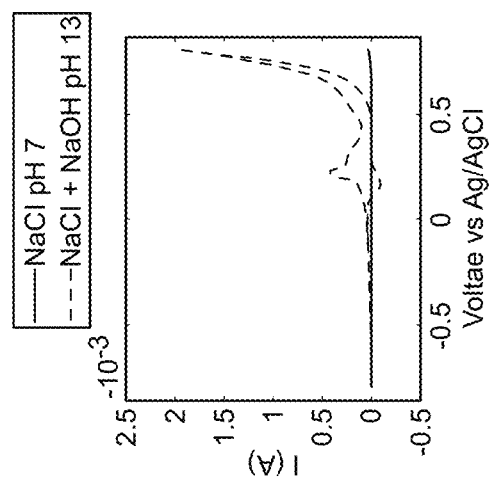
FIG. 8B is plot of current versus voltage demonstrating the cyclic voltammetry of a nanoporous Au/$Co_3O_4$ contact in 0.1M NaCl at pH 7 and 0.1M NaCl+0.1M NaOH (pH 13) containing 10 mM glucose, according to an embodiment of the present invention.
Figure 8E:
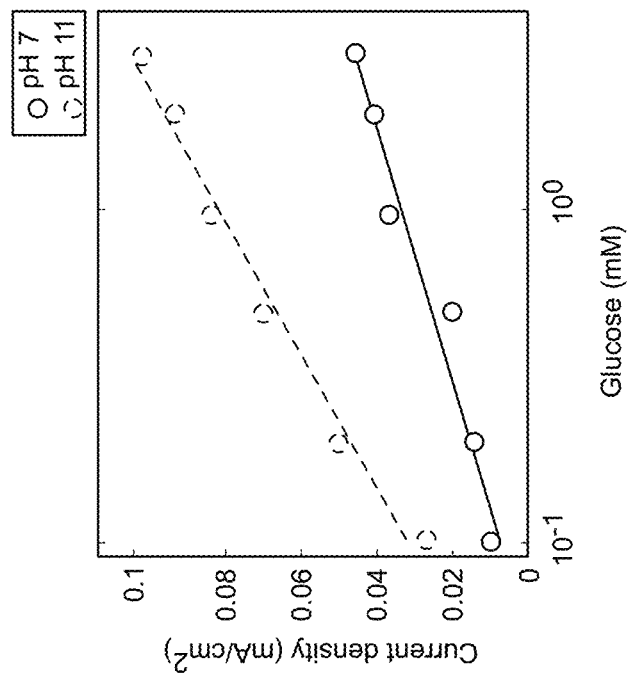
FIG. 8E is a Log plot of current density $I_g$ versus glucose concentration sampled after $V_{pH}=-1V$ for 100 seconds, according to an embodiment of the present invention.
Figure 8D:
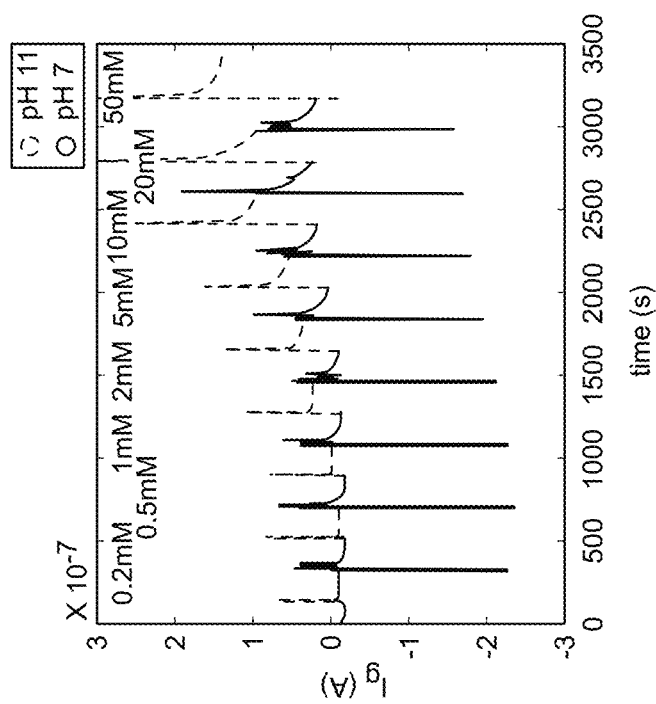
FIG. 8D shows a plot of the current versus time to illustrate the current response of device at a constant voltage $V_g=0.5V$ over increasing concentrations of glucose in 0.1M NaCl solution, according to an embodiment of the present invention.

FIG. 8A is a schematic diagram depicting a sensing mechanism of cobalt oxide contacts, according to an embodiment of the present invention. At pH=7, the contact is primarily $Co_3O_4$, which does not oxidize glucose. In alkaline conditions (pH>11), the contact is now mainly $CoO_2$, $CoO_2$ species react with glucose and are converted to COOH. This CoOH is then oxidized back to $CoO_2$. For every oxidized glucose molecule, the contact collects two electrons measured as $I_g$. FIG. 8B is plot of current versus voltage demonstrating the cyclic voltammetry of a nanoporous Au/$Co_3O_4$ contact in 0.1M NaCl at pH 7 and 0.1M NaCl+0.1M NaOH (pH 13) containing 10 mM glucose, according to an embodiment of the present invention. FIG. 8C is a plot of pH measurements versus time, according to an embodiment of the present invention. FIG. 8C shows the pH measurements of 0.1M NaCl (initial pH=7) after pH modulation with Pd electrode with a −1V potential between 10 seconds and 5 minutes. FIG. 8D shows a plot of the current versus time to illustrate the current response of device at a constant voltage $V_g$=0.5V over increasing concentrations of glucose in 0.1M NaCl solution, according to an embodiment of the present invention. As shown in FIG. 8D, Pd contacts cycle the pH between pH 7 ($V_{pH}$=0.3V) and pH 11 ($V_{pH}$=−1V). During the pH 7 phase, glucose concentration is stepped. FIG. 8E is a Log plot of current density $I_g$ versus glucose concentration sampled after $V_{pH}$=−1V for 100 seconds, according to an embodiment of the present invention. As expected by Langmuir isotherm, in $I_g$ is linear with glucose concentration with higher $I_g$ for higher pH. Cobalt oxide is deposited on the gold surface as $Co_3O_4$ and, in solution, undergoes a series of oxidation reactions with hydroxide, as shown in FIG. 8A. These reactions increase the oxidation state from Co(II/III) to Co(III) and Co(IV), respectively:

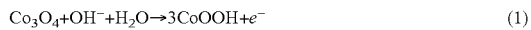
$$Co_3O_4 + OH^- + H_2O \rightarrow 3CoOOH + e^- \quad (1)$$

and

$$CoOOH + OH^- \rightarrow Co_2O_2 + H_2O + e^- \quad (2)$$

While both $Co_3O_4$ and CoOOH species can oxidize glucose, the primary mechanism for oxidation of glucose to gluconolactone in cobalt oxide sensors involves two Co(IV) atoms in the reaction:

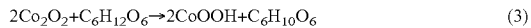
$$2Co_2O_2 + C_6H_{12}O_6 \rightarrow 2CoOOH + C_6H_{10}O_6 \quad (3)$$

Figure 9:
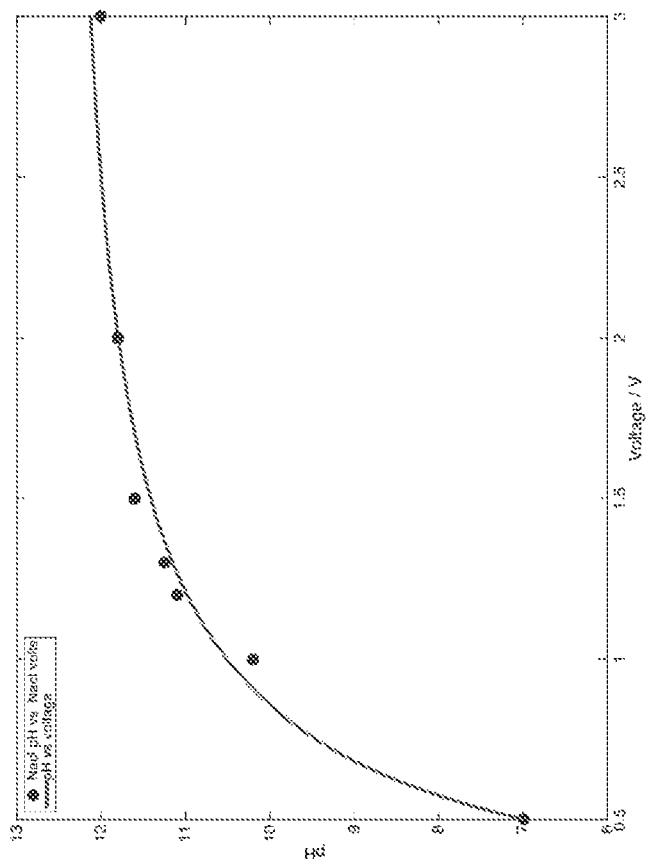
FIG. 9 is a plot of the measured pH as a function of voltage, according to an embodiment of the present invention.
Figure 10:
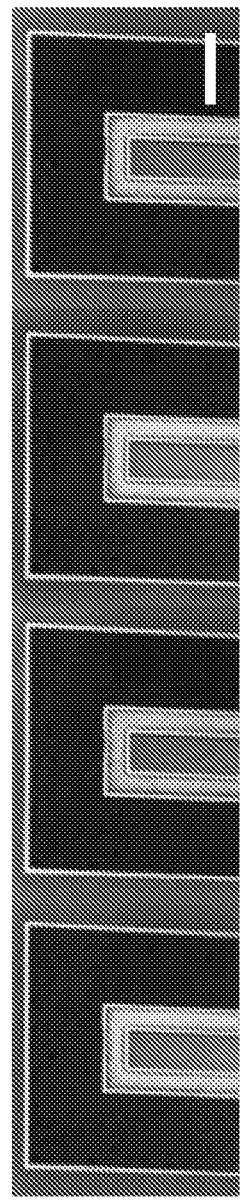
FIG. 10 shows pH changes detected optically with pH indicator solution, according to an embodiment of the present disclosure.

In equation (3), two Co(IV) atoms are reduced to Co(III) as CoOOH. These CoOH species are in turn oxidized back to $Co_2O_2$, for each Co(III) oxidized to Co(IV), an electron is collected by the cobalt oxide contact and is recorded as current (Ig). At neutral pH, the concentration of hydroxide species necessary to create Co(IV) is low thus greatly limiting the glucose oxidation reaction kinetics. At high pH, as shown in FIG. 8A, the cobalt surface contains many more Co(IV) and the glucose oxidation reaction is faster allowing glucose detection at lower concentrations respect to neutral pH. For this reason, metal oxide sensors and many other inorganic sensors that directly oxidize glucose operate at high pH. The inventors performed current voltage measurements (CV) using a $Co_3O_4$ contact in a solution containing 10 mM glucose at pH 7 (FIG. 8B, black lower trace) and pH 13 (FIG. 8B, upper trace). From the CV it is clear that the glucose oxidation reaction at pH 7 is barely occurring, while at pH 13 in 0.1M NaOH the peak associated with oxidation of glucose by the $Co_2O_2$ occurs at V=0.5V, as expected. In order to mimic the alkaline conditions found when the glucose sensor is immersed in 0.1M NaOH, the inventors perform pH control in proximity to the cobalt oxide contact using the palladium contact with $V_{pH}$=−1 V for different amounts of time (t), as shown in FIG. 8C. For t<300 s the pH increases with time because more $H^+$ are able to transfer from the solution to the Pd contact. However, at t=300 s the solution pH saturates because there are less $H^+$ available in the solution to transfer into the Pd. Even with lower $V_{pH}$=−3V the solution pH saturates at pH=11. FIG. 9 is a plot of the measured pH as a function of voltage, according to an embodiment of the present invention. FIG. 9 shows that a pH of 0.1 ml volume of 0.1M NaCl solution after 120 s of pH change. This pH change is reversible, as shown in FIG. 10. FIG. 10 shows pH changes detected optically with pH indicator solution, according to an embodiment of the present disclosure. The palladium contact (black) cycled between −1V and +0.3V vs an AgCl pellet electrode for 1 minute at each voltage. The solution switched between an initial neutral solution (yellow) at t=0 s (left), to basic pH (blue) at t=60 s after 1 minute of −1V on the Pd (second from left). The cycle was repeated neutral conditions at t=120 s after +0.3V on the Pd, and basic conditions at t=180 s. The scale depicted by the white bar is equal to 0.4 mm.

In an embodiment, the inventors selected a $V_{pH}$ at approximately −1V or −1.1V for glucose sensing. This $V_{pH}$ value corresponds to a solution pH=11. For glucose detection, the inventors measure the current at the cobalt oxide sensing contact ($I_g$) with $V_g$=0.5V (as shown in FIG. 8D). $V_g$=0.5V corresponds to the maximum glucose oxidation peak, as observed in FIG. 8B. During the measurement, the solution cycles pH from neutral pH ($V_{pH}$=0.3 V) to pH=11 ($V_{pH}$=−1 V). At neutral pH, Ig is very small for low glucose concentrations below 1 mM. However, for pH=11 Ig raises above the noise level and the device can detect glucose in concentrations from 0.2 mM to 10 mM during periods of pH 11 ($V_{pH}$=−1V).

The inventors collected $I_g$ data for each concentration after 120 seconds of changing pH and plotted it against glucose concentration both at pH=7 and pH=11 (FIG. 8D). This data indicates that the glucose oxidation reaction is more efficient at pH=11. Additionally, the data can be fit with the Langmuir isotherm corresponding to the absorption of glucose at different pH. At pH 11, the reaction rate is higher because there are more Co (IV) species available to oxidize the glucose.

To demonstrate the feasibility of the non-enzymatic cobalt oxide glucose sensor in real world continuous glucose monitoring to real world measurements, the inventors developed a prototype low-cost and low-power miniature board that can apply voltage excitation, record and condition the signal as well as transmit it to an external device (WI-FI) for storage and post processing. FIG. 11A is a photograph of the low-cost and low-power miniature board used to provide the excitation and measure the current generated by the chemical reaction to determine the glucose level, according to an embodiment of the present disclosure. The board includes two layers (sides). The board includes a WIFI enabled microcontroller, a multiplexer, an amplifier, and analogue to digital converter, and two batteries. We connect the board to the cobalt oxide, palladium, and silver/silver chloride contacts to the input and outputs of the board. The WIFI-enabled microcontroller (for example, Espressif Systems microcontroller ESP8266) is installed on the "front" side while the rest of the electronics on the "back" side. This include: (i) an analog amplifier INA122U Texas Instruments, (ii) a 16-bit analog-to-digital converter (ADS1115—Texas Instruments), (iii) a multiplexer (Texas Instruments TS5a4624) which together with a fixed +1.4V power supply circuit (ABLIC S-13R1A14) and an adjustable (+0.1 to +3.2V) adjustable power supply circuit (Microchip MCP6010T) to generate the voltages required for the excitation (+0.3V and -1.1V), (iv) a power supply (Microchip MCP601OT) for the sensing circuit, (v) two opto-isolator components (Vishay Semiconductor VOS618A) to separate the sensing and excitation sides of the circuit board.

Figure 11B:
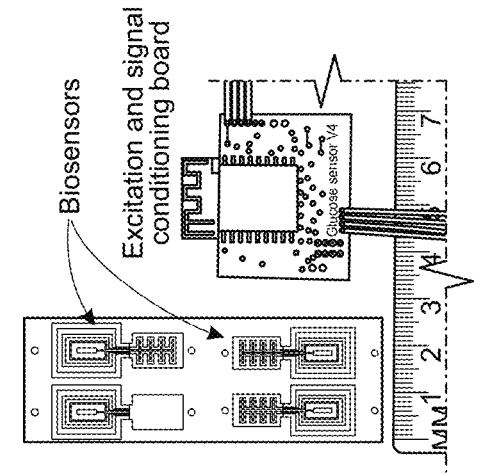
FIG. 11B depicts the biosensor (left) and the microcontroller signal conditioning/sensing board (right) that applies the voltage inputs, extracts and amplifies the sensing current, and transmits the results via WIFI for further analysis, according to an embodiment of the present disclosure.

FIG. 11B depicts the biosensor (left) and the microcontroller signal conditioning/sensing board (right) that applies the voltage inputs, extracts and amplifies the sensing current, and transmits the results via WIFI for further analysis, according to an embodiment of the present disclosure. In term of size, it is noted that one microscope slide fits 4 experimental biosensors. FIG. 11C is a high level circuit schematic showing how the components shown in FIG. 11A are integrated with the biosensor, according to an embodiment of the present disclosure. A high level schematic of the sensor and associated electronic circuitry are presented in FIGS. 11B and 11C with a more detailed circuit schematic present in the supporting information in FIG. 12. The board features two electronic circuits, which are isolated from each other and each of them has an adjustable power circuit. The first circuit supplies $V_g$ (from 10 mV to 3.2 V) to the cobalt oxide contact and the second circuit supplies $V_{pH}$ (from -1.1 V to 0.3 V) to create the alkaline conditions for glucose sensing to occur. A WIFI-enabled microcontroller (ESP8266) and a 16-bit analog-to-digital converter was used to measure Ig, which is the current generated by the glucose oxidation reaction and is required to measure the glucose concentration.

Figure 12:
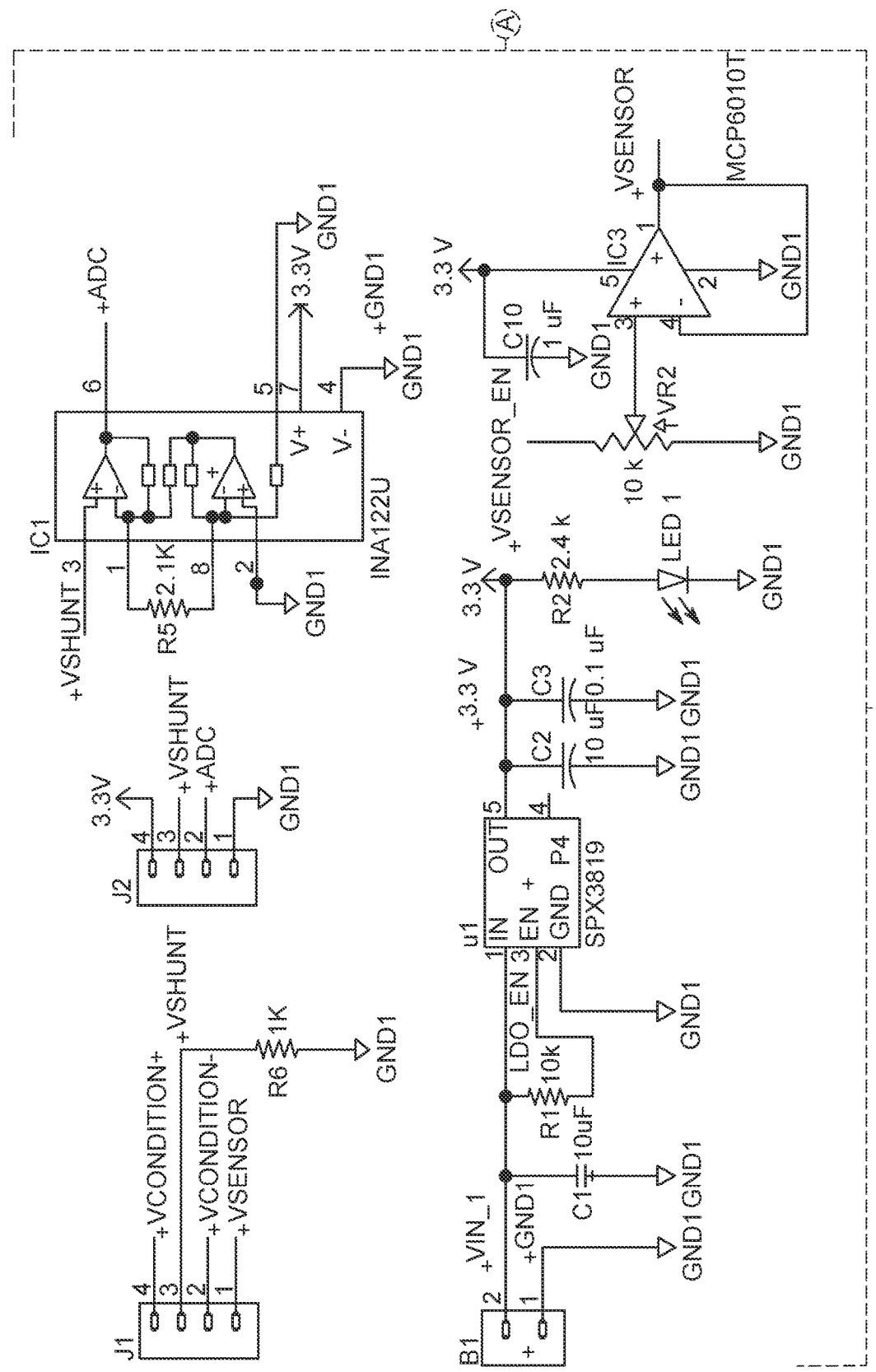
FIG. 12 depicts detailed circuit logic schematics of the sensor unit, according to an embodiment of the present disclosure.
Figure 12:
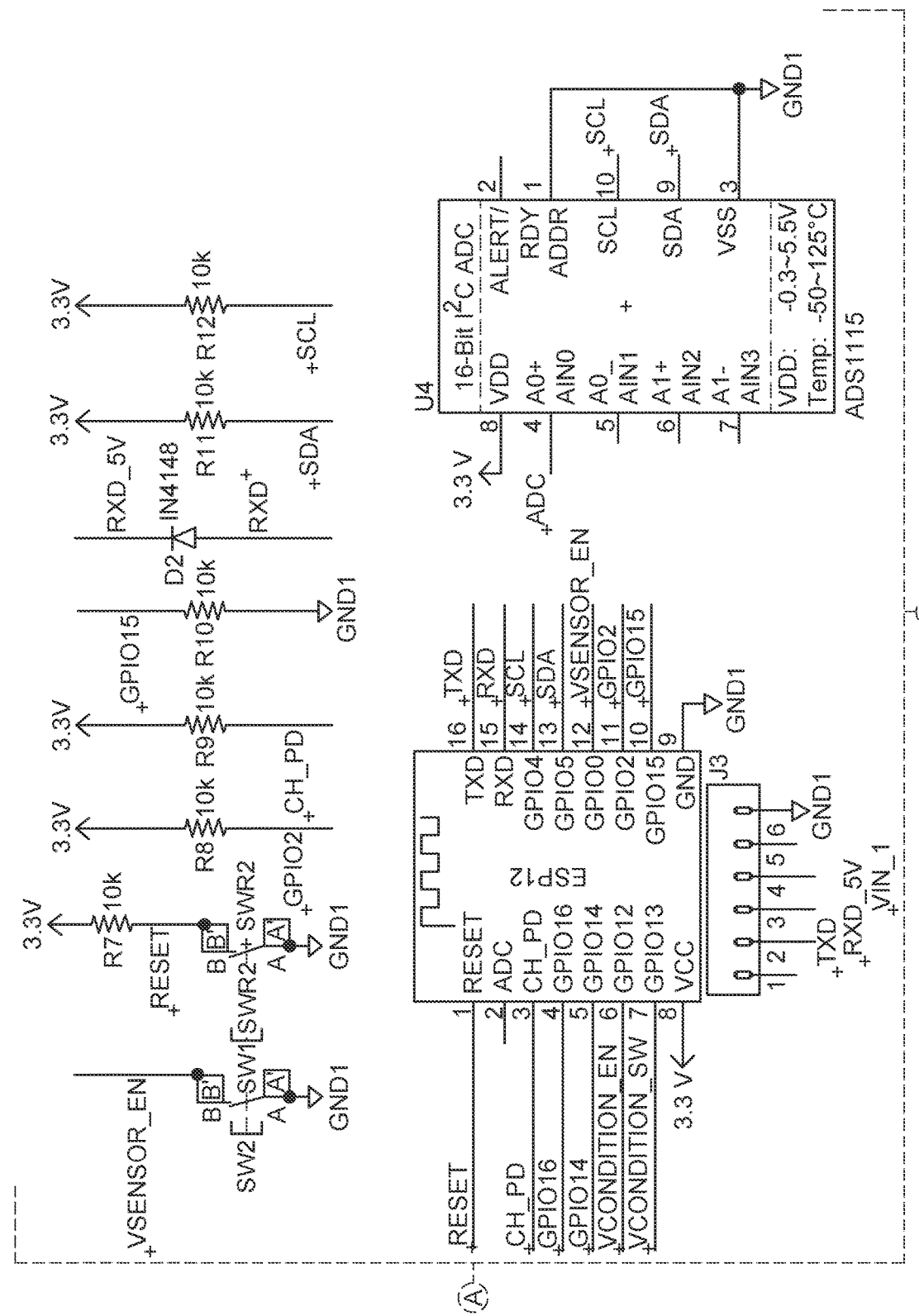
Figure 12:
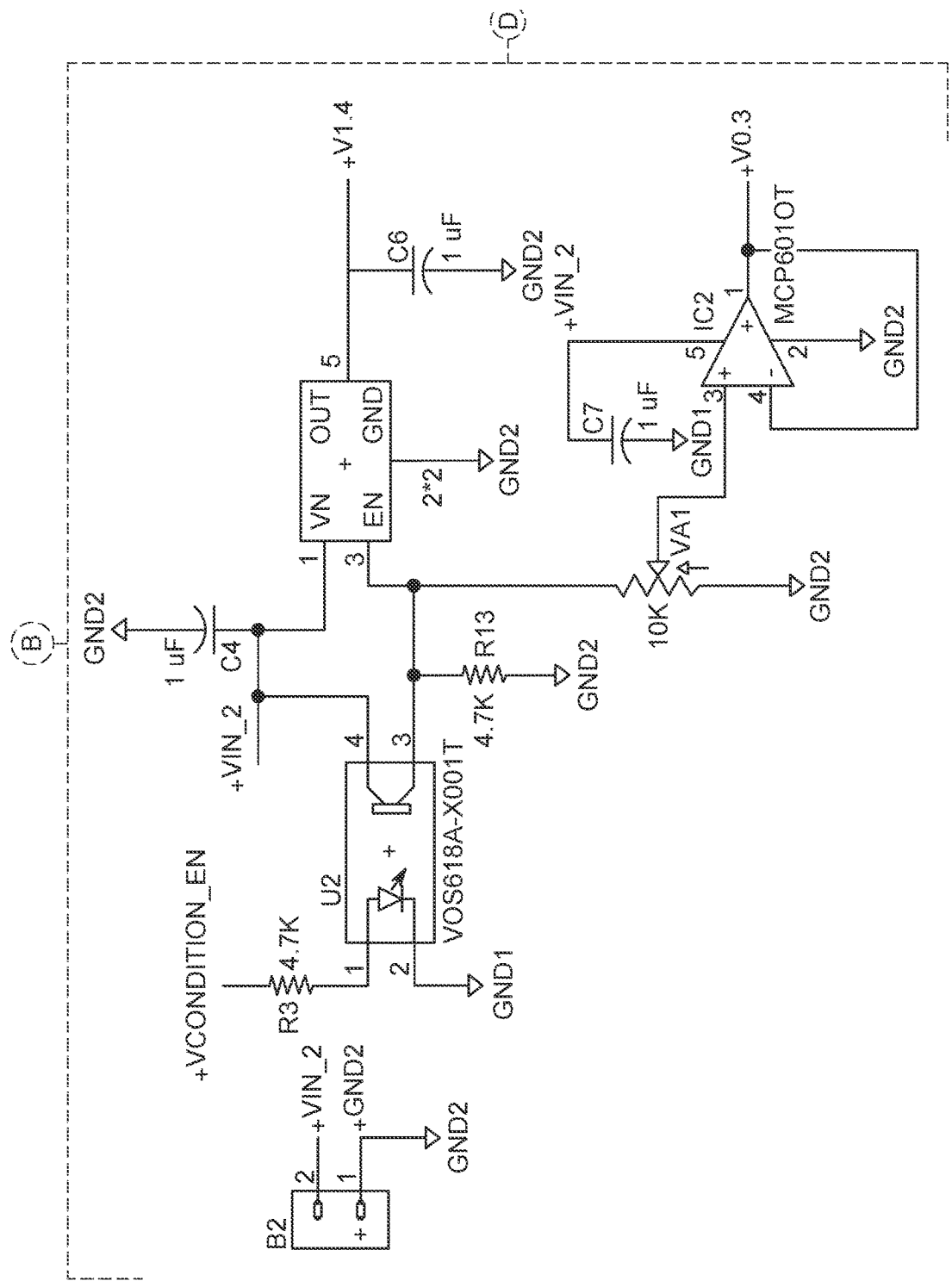
Figure 12:
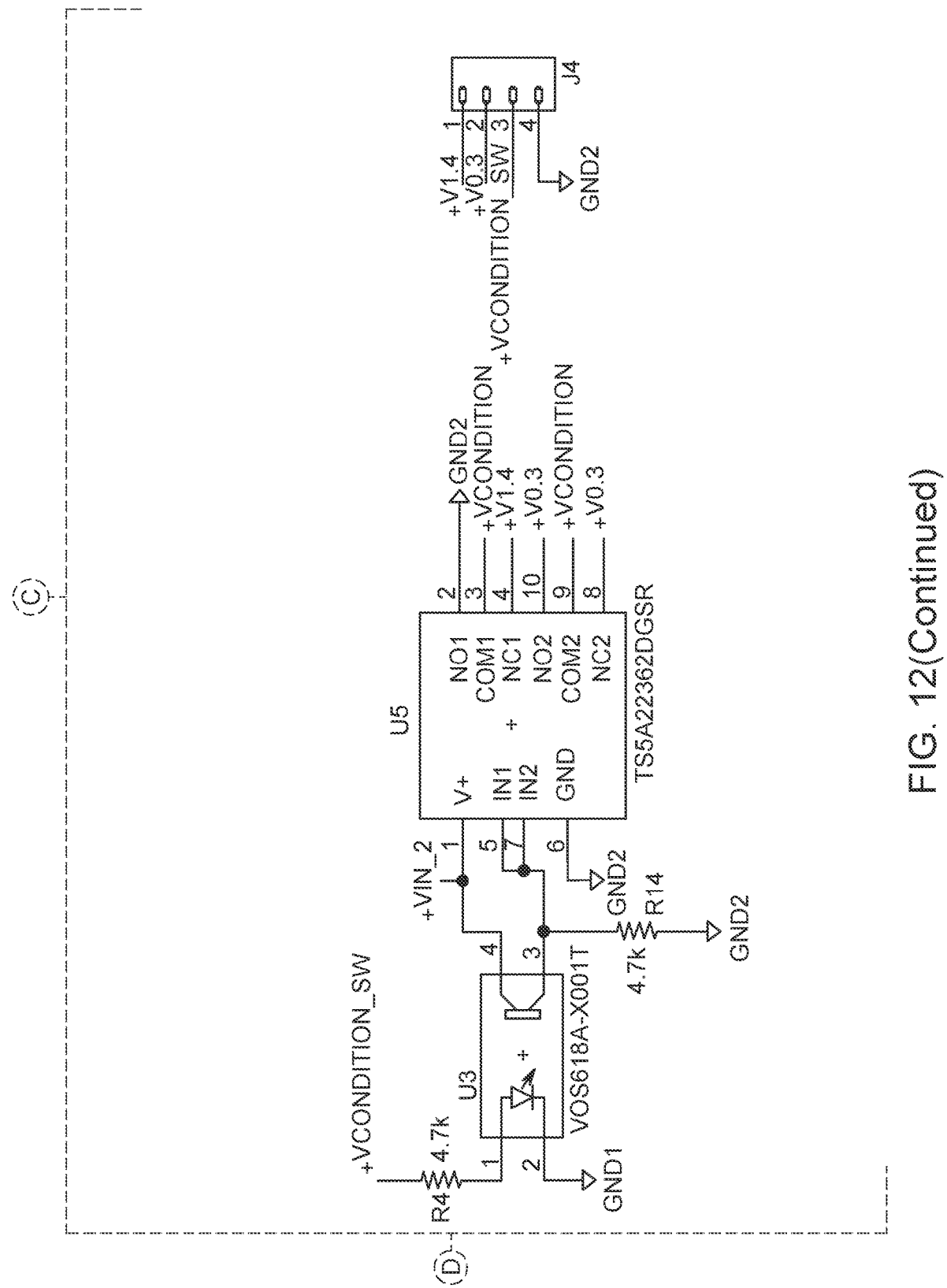

FIG. 12 depicts detailed circuit logic schematics of the sensor unit, according to an embodiment of the present disclosure. PSU is generated from voltage divider on a high precision potentiometer (VR2) which later buffers through unify gain op-amp. R6, resistor is connected in-line with the sensor unit, its work as shunt resistor that converts current to voltage. The voltage across R6 is amplified with a gain of 100 by INA122U, instrument amplifier which latter sense by ADS1115, 16-bits analog to digital converter. Similar to the sensor unit PSU, part of pH PSU use potentiometer (VR1) and unify gain op-amp to create one of the signals. The second signal is created from a 1.4 V voltage regulator. Down the line, the two signals are multiplexed through TS5A22362DGSR, analog multiplexer for pH PSU output. Both PSU can be enabled/disabled by the microcontroller. Moreover, pH PSU is isolated from the microcontroller due to different battery and VOS618A, opto-isolator.

Figure 11D:
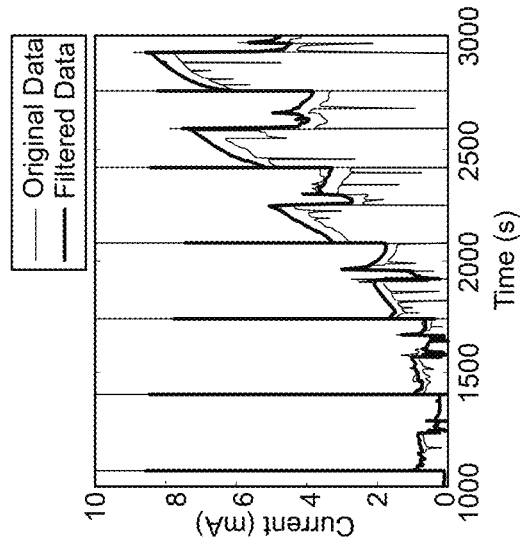
FIG. 11D shows the experimental results from the glucose sensor measuring increasing concentrations of glucose in a NaCl solution made to mimic human sweat, according to an embodiment of the present invention.
Figure 11A:
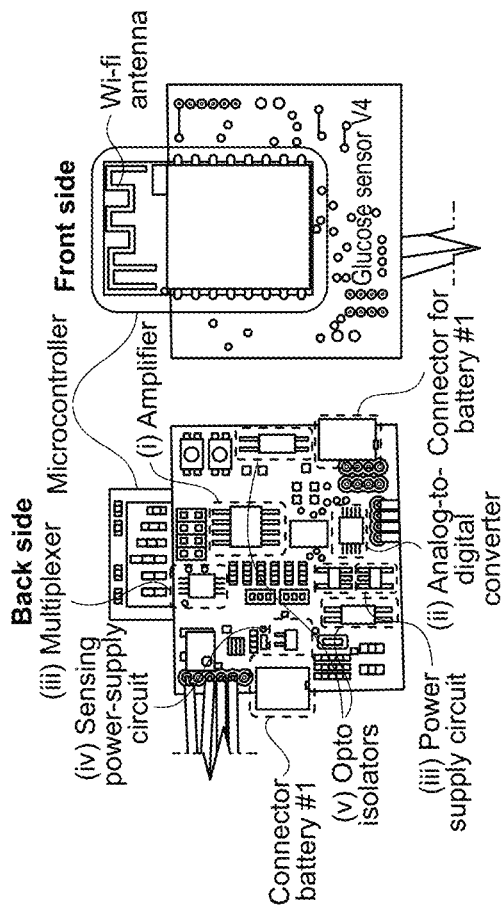
FIG. 11A is a photograph of the low-cost and low-power miniature board used to provide the excitation and measure the current generated by the chemical reaction to determine the glucose level, according to an embodiment of the present disclosure.
Figure 11C:
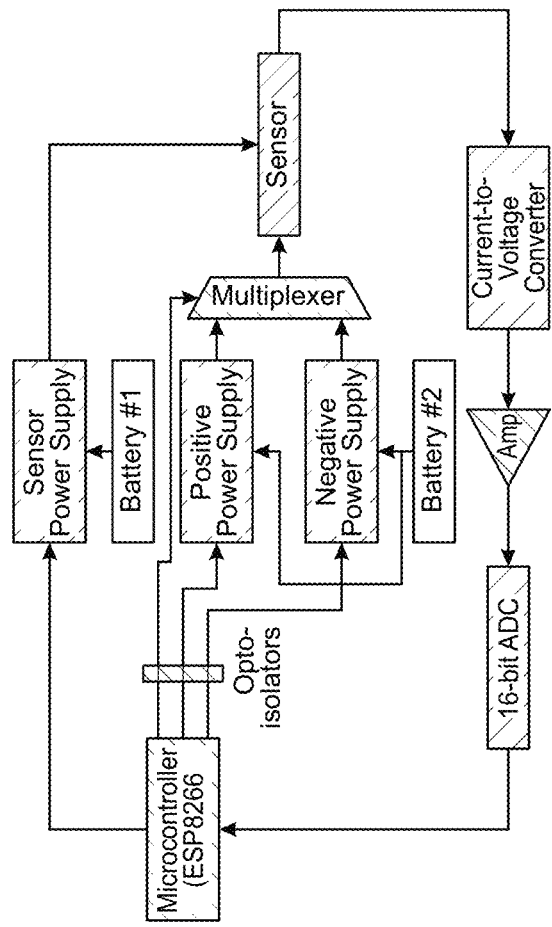
FIG. 11C is a high level circuit schematic showing how the components shown in FIG. 11A are integrated with the biosensor, according to an embodiment of the present disclosure.

FIG. 11D shows the experimental results from the glucose sensor measuring increasing concentrations of glucose in a NaCl solution made to mimic human sweat, according to an embodiment of the present invention. FIG. 11D shows Ig vs time recording with microcontroller from sensing at 0 mM, 0.1 mM, 0.2 mM, 0.5 mM, 1 mM, 2 mM, 3 mM glucose concentration in 0.1M NaCl solution. This $I_g$ data was filtered by the conditioning board to remove noise and it was recorded with the PC wirelessly connected to the microcontroller. FIG. 11D shows the measured current as a function of time in seconds (gray) as well as the filtered signal using a moving average filtering technique with a ⅓ of a second window (black). The data is consistent with what was acquired with the bulkier and non-portable potentiostat and semiconductor parameter analyzer and follows an analogous calibration curve with different $I_g$ levels than presented in FIG. 8E.

The inventors fabricated a non-enzymatic metal oxide glucose sensor that is able to detect physiologically relevant glucose levels in neutral bodily fluids such as sweat and tears. This sensor is superior to other metal oxide glucose sensors because it does not require an alkaline fluid for operation. To sense glucose in neutral fluids, this sensor induces a localized and reversible pH change with a Pd contact that absorbs $H^+$ from the neutral fluid and increases the pH. This flexibility allows for the seamless integration with current glucose sensing platforms such as contact lenses and skin patches. In comparison to the current enzymatic sensors, the present metal oxide sensor does not suffer from limited lifetime due to enzyme degradation over time. This strategy of controlling local pH to enable sensing in neutral biological fluid is broadly applicable to other metal oxide and oxidative inorganic sensors for biologically relevant analytes including but not limited to ascorbic acid, dopamine, glycerol, ethylene glycol, and nitrite.

Glucose Sensor Fabrication:

In an embodiment, glass slides are sonicated for 20 min in 80% v/v acetone and 20% v/v iso-propanol (IPA), and dried with N2. S1813 photoresist (from Dow Chemicals Corporation) was deposited on top of the glass substrates, following standard protocols (Spin-coated at 3000 RPM, baked 1 min. at 110 Celcius), to create the Au patterns. In an embodiment, A 5 nm Ti adhesion layer and a 120 nm thick Au layer were evaporated on glass microscope slides. Deposition of photoresist was repeated prior to each electrodeposition following the same process. In an embodiment, to increase the sensitivity of the sensor, the inventors increased the surface area of Au strip.

Figures 13A, 13B:
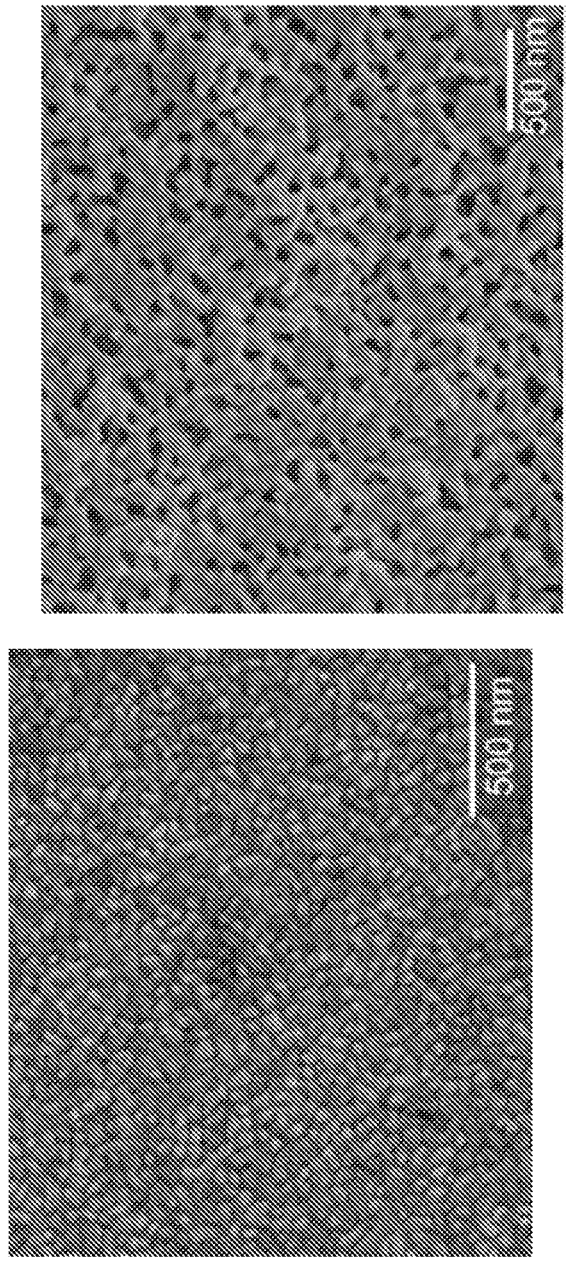
FIGS. 13A and 13B show gold (Au) etch scanning electron microscope (SEM) images of an un-etched gold and a nanoporous gold etched with $ZnCl_2$ in Benzyl Alcohol at 120° C., respectively, according to embodiments of the present invention.
Figure 14:
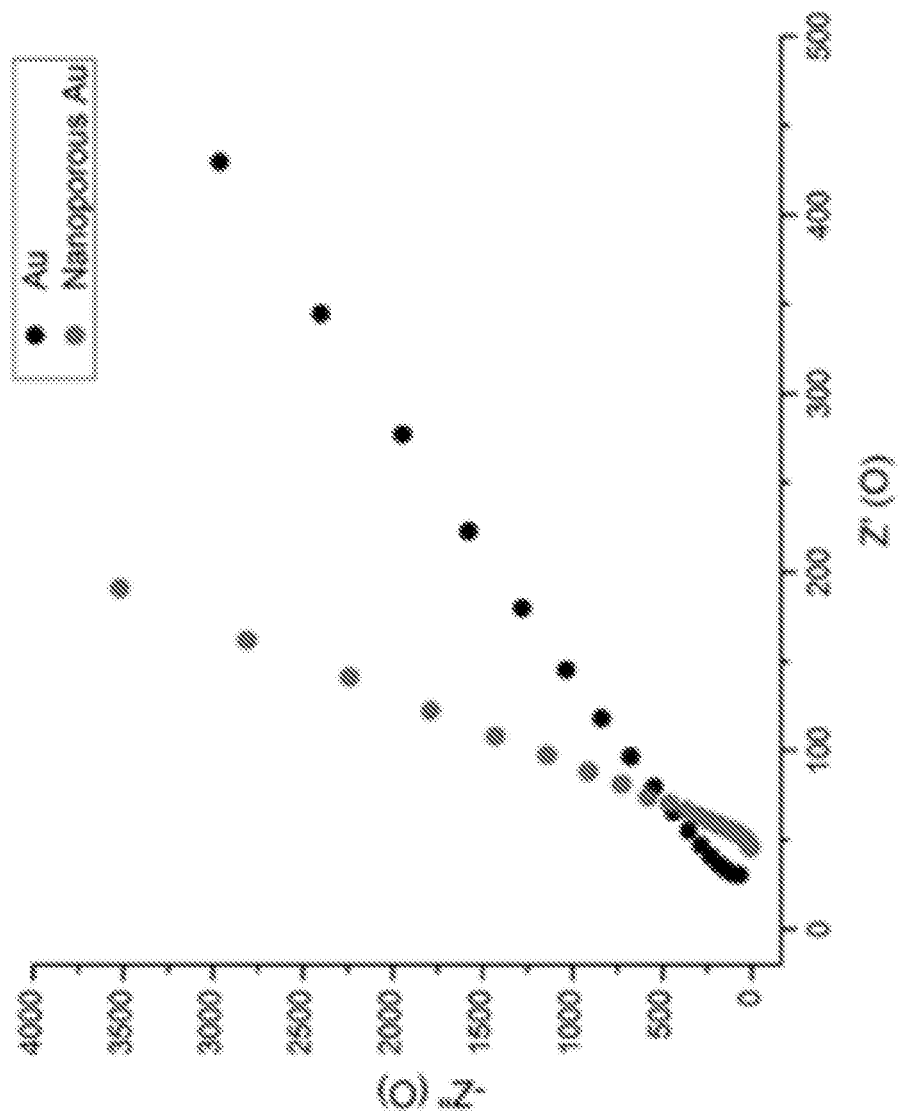
FIG. 14 is a Au vs nanoporous Au Nyquist plot generated from impedance spectroscopy measurements showing that the nanoporous Au has a higher capacitance evident by the larger value of the imaginary impedance, according to an embodiment of the present invention.

FIGS. 13A and 13B show gold (Au) etch scanning electron microscope (SEM) images of an un-etched gold and a nanoporous gold etched with $ZnCl_2$ in Benzyl Alcohol at 120° C., respectively, according to embodiments of the present invention. The bars in the images indicats the scale of 500 nm. In an embodiment, nanoporous Au is produced by electrochemically etching the 100 nm thick Au layer with a solution of 1.5M $ZnCl_2$ in Benzyl Alcohol at 120° C. In an embodiment, two cycles of a cyclic voltammetry routine from -0.4V to 1.7V vs AgCl is performed with Zn wire reference and counter electrodes and a Metrohn Autolab Potentiostat (PGSTAT128N). This routine corresponds to two rounds of Zn—Au alloying/dealloying. The devices are then washed with 0.1M $H_2SO_4$, IPA, and di-water. In an embodiment, this treatment is only performed on the contact destined for cobalt oxide. The nanporous Au has higher capacitance resulting from a larger surface area, as shown in FIG. 14. FIG. 14 is a Au vs nanoporous Au Nyquist plot generated from impedance spectroscopy measurements showing that the nanoporous Au has a higher capacitance evident by the larger value of the imaginary impedance, according to an embodiment of the present invention.

Figure 15A:
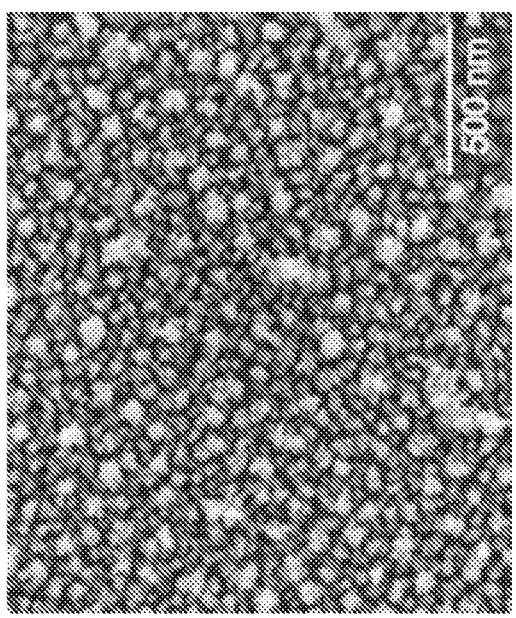
FIGS. 15A and 15B are scanning electron microscope images of Pd nanoparticles and Ag/AgCl nanoparticles, respectively, according to embodiments of the present invention.
Figure 15B:
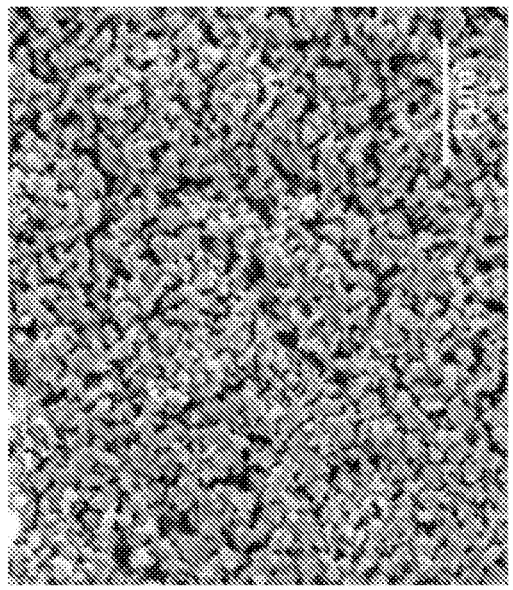

In an embodiment, to create the cobalt oxide contact, The inventors electrodeposited on Au using a three-electrode electrochemical cell setup with Pt counter and AgCl glass reference electrodes. Cobalt Oxide is deposited from a solution of 5 mM Cobalt(II) Nitrate suspended in 0.1M $H_2SO_4$. A CV routine (-1.2V to -0.2V) with a glass AgCl reference electrode and a Pt wire counter electrode. This was performed with a Metrohn Autolab Potentiostat (PGSTAT128N). In an embodiment, to deposit Pd, the inventors used 10 wt. % Palladium Nitrate ($PdNO_3$), purchased from Sigma Aldrich. This was diluted with deionized water to give a 1 wt. % $PdNO_3$ solution. Pd NPs were electrochemically deposited onto the Pd contacts using a DC voltage of V=-0.3V with a deposition time of 3 seconds with a glass AgCl reference and Pt counter electrode. FIGS. 15A and 15B are scanning electron microscope images of Pd nanoparticles and Ag/AgCl nanoparticles, respectively, according to embodiments of the present invention. This resulted in a darkening of the contacts where the NPs were successfully deposited. The Pd nanoparticles have an increased surface area which greatly enhances the pH change effect over planar Pd and area stable over many pH cycles (FIGS. 16 and 17).

Figure 16:
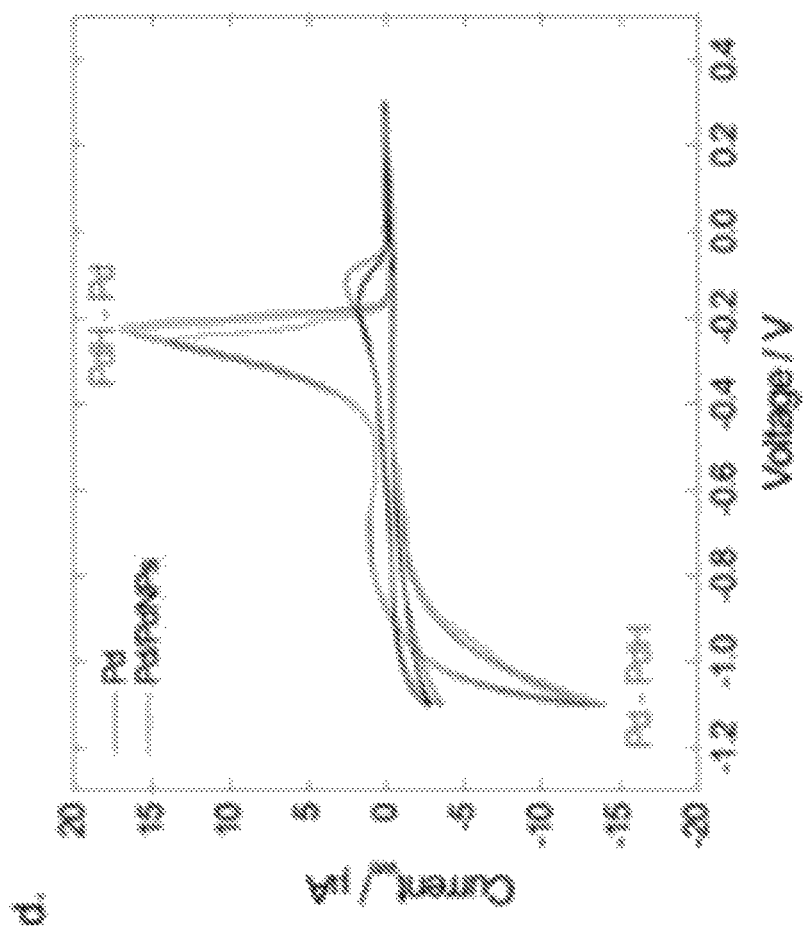
FIG. 16 is a plot of current versus voltage for Pd and Pd/PdNPs showing cyclic voltammetry of a Pd contact versus Pd nanoparticles contact, according to an embodiment of the present invention.
Figure 17:
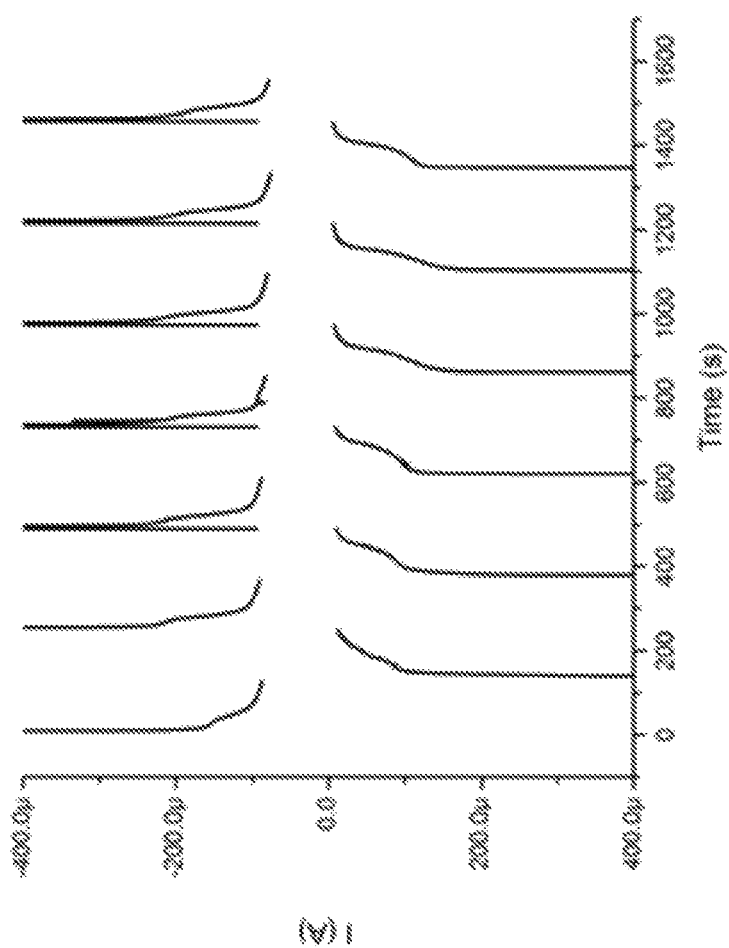
FIG. 17 is a plot of the current versus time from the Pd contact during pH cycling, according to an embodiment of the present invention.

FIG. 16 is a plot of current versus voltage for Pd and Pd/PdNPs showing cyclic voltammetry of a Pd contact versus Pd nanoparticles contact, according to en embodiment of the present invention. The plot shows the increased performance of electrodeposited Pd. The current which corresponds to the $H^+$ transfer between solution and Pd is higher for electrodeposited Pd. FIG. 17 is a plot of the current versus time from the Pd contact during pH cycling, according to an embodiment of the present invention. The Pd contact is switched between $-1V$ and $+0.3V$ vs AgCl. The current is reproducible for multiple cycles.

In an embodiment, to create the Ag/AgCl electrode, the inventors electrodeposit Ag on top of the Au contact in the reservoir, by using a solution containing 50 mM of $AgNO_3$ and 0.2 M sulfuric acid in di-water, by using a constant current of 0.5 mA for 150 seconds (outer contact) and 0.15 mA for 150 s (inner contact). A glass Ag/AgCl electrode is used as a reference electrode and Pt wire was used as a counter electrode. CV is used to form silver chloride on the Ag, by using a solution containing 0.5 M NaCl in di-water. 5 cycles are carried from $-0.5$ to 0.9 V with a scan rate of 50 mV/second.

Figure 18:
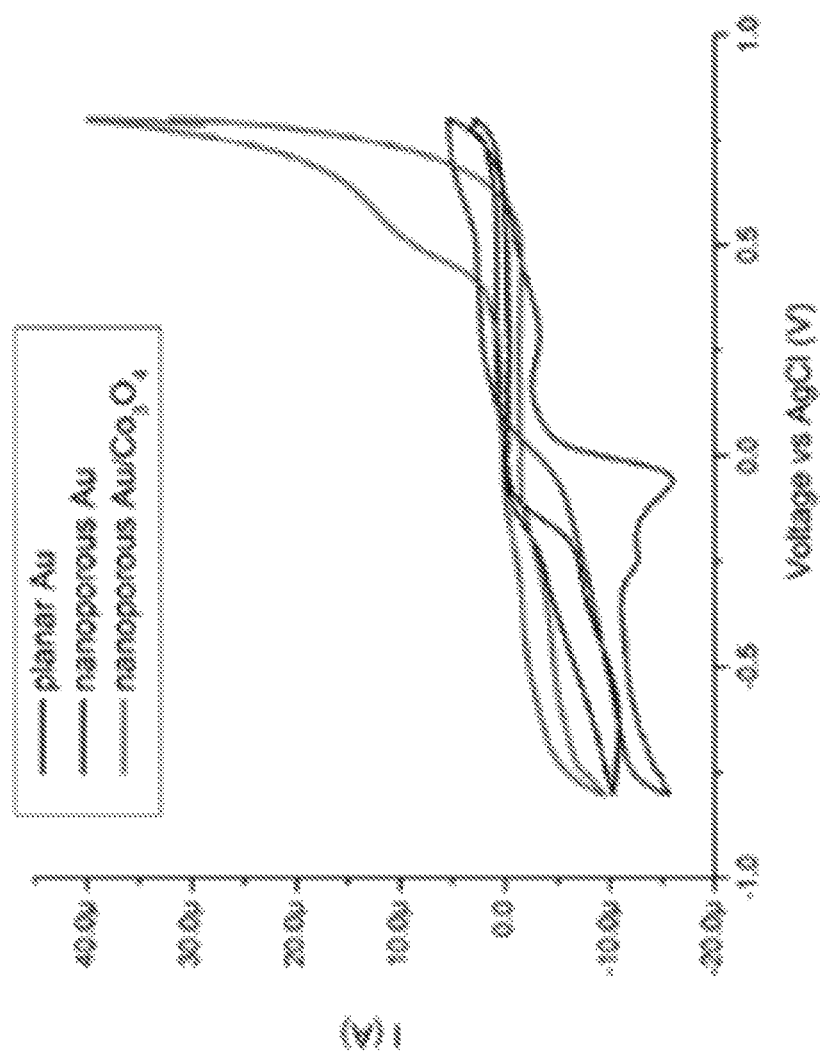
FIG. 18 is a plot of current versus voltage for planar Au, nanoporous Au and nanoporous Au/Co$_3$O$_4$ in 0.1M NaCl in the absence of glucose, according to embodiments of the present invention.

Characterization of Cobalt Oxide Contact:

In an embodiment, the planar Au, nanopourous-etched Au, and nanoporous $Au/Co_3O_4$ coated surfaces are characterized by cyclic voltammetry in 0.1M NaCl solution (pH 7) vs. a glass AgCl electrode. FIG. 18 is a plot of current versus voltage for planar Au, nanoporous Au and nanoporous $Au/Co_3O_4$ in 0.1M NaCl in the absence of glucose, according to embodiments of the present invention. A CV current typical gold profile (curve labeled "planar Au") is amplified when the surface area of the contact is increased after etching (curve labeled "nanoporous Au"). After deposition of $Co_3O_4$, the recorded current is lower than that of the nanoporous Au as a result of the oxide film being more resistive (curve labeled "nanoporous $Au/Co_3O_4$") is true until a broad peak at 0.5V which is characteristic of further oxidation of $Co_3O_4$.

pH Control and Characterization:

In an embodiment, pH cycling is controlled with an Autolab potentiostat connected to the Pd contact and an external AgCl pellet. The quantification of solution pH is recorded with a micro-pH meter (from Fisher Scientific). Diffusion of pH in is recorded with a Keyence VHX-5000 series digital microscope. The solution is 0.1M NaCl initially at pH 7 with a universal pH indicator dye (from Fisher Chemical) at a volume of 0.1 mL.

Glucose Measurements—NI and Potentiostat:

In an embodiment, pH cycling is controlled by an Autolab potentiostat connected to the on-chip Pd and AgCl electrodes. The on-chip cobalt oxide-AgCl circuit is controlled with an NI PXI with a digital multimeter and source measuring unit. Measurements began initially in 0.1M NaCl in di-water, glucose concentration is increased during periods of pH 7.

Glucose Measurements—Microchip:

In an embodiment, measurements are performed between the on-chip Pd contact and an external AgCl pellet and the on-chip $Co_3O_4$ contact and an external AgCl pellet. Measurements begin initially in 0.1M NaCl in di-water, glucose concentration was increased during periods of pH 7.

Electrical Characterization (CV):

In an embodiment, device characterization is performed utilizing both an Autolab potentiostat and national instruments (NI) PXI with a digital multimeter (DMM) and a source measurement unit (SMU). A custom labview program is controlling the NI system. Potentiostat tests are run to gauge the performance of the devices, cyclic voltammetry, and frequency response analysis (FRA).

In an embodiment, the inventors created nanoporous Au through electrochemical alloying/dealloying of Au—Zn using zinc chloride ($ZnCl_2$) in benzyl alcohol. The process employed is adapted from a Zn etch for etching gold wires to create highly sensitive glucose sensors. As expected, the nanoporous Au has higher capacitance resulting from a larger surface area and thus, a higher sensitivity to glucose concentration. In an embodiment, to improve the performance of the nanoporous Au, cobalt oxide is electrodeposited on its surface in a one-sweep cyclic voltammetry routine from ($-0.2$ to $-1.2V$) on the Au contact in a three-electrode set up with a glass AgCl reference and Pt counter electrode in a 0.1M cobalt nitrate solution. In an embodiment, prior to electrodeposition, the nanoporous Au contact that is exposed to the cobalt nitrate is patterned with a photoresist in order to define its area and the rest of the Au contacts to be insulated in order to avoid contamination between the electrodes. In an embodiment, the patterning process was repeated for the electrodeposition of the other metals (Pd, Ag). Pd is electrodeposited in by a constant negative voltage ($V=-0.3V$) in the presence of a Pd nitrate solution. The Pd exhibited high surface area that improves the $H^+$ transfer into its structure, and thus the pH modulation. Finally, Ag is electrodeposited at a constant current ($I=-500$ μA) for 150 sec for the big $AgCl_{out}$ electrode, and ($I=-150$ μA) for 150 sec for the smaller $AgCl_{in}$ electrode. The Ag is converted to AgCl by performing a 5 cycle CV between $-0.5V$ to 0.9V in the presence of 0.5M NaCl. During the chlorination the color of the Ag changed from silver-white to dark grey.

REFERENCES

[1] C. f. D. C. a. Prevention, Atlanta, GA: Centers for Disease Control and Prevention, US Dept of Health and Human Services 2017.

[2] P. Zimmet, K. G. Alberti, D. J. Magliano, P. H. Bennett, Nat Rev Endocrinol 2016, 12, 616.

[3] A. J. Bandodkar, J. Wang, Trends in Biotechnology 2014, 32, 363.

[4] E. Witkowska Nery, M. Kundys, P. S. Jelen, M. Jonsson-Niedziolka, Anal Chem 2016, 88, 11271.

[5] W. Gao, S. Emaminejad, H. Y. Y. Nyein, S. Challa, K. V. Chen, A. Peck, H. M. Fahad, H. Ota, H. Shiraki, D. Kiriya, D. H. Lien, G. A. Brooks, R. W. Davis, A. Javey, Nature 2016, 529, 509.

[6] H. Yao, Y. Liao, A. R. Lingley, A. Afanasiev, I. Lahdesmaki, B. P. Otis, B. A. Parviz, Journal of Micromechanics and Microengineering 2012, 22, 075007.

[7] A. J. Bandodkar, J. Wang, Trends Biotechnol 2014, 32, 363.

[8] J. Kim, A. S. Campbell, J. Wang, Talanta 2018, 177, 163.

[9] A. Martin, J. Kim, J. F. Kurniawan, J. R. Sempionatto, J. R. Moreto, G. D. Tang, A. S. Campbell, A. Shin, M. Y. Lee, X. F. Liu, J. Wang, Acs Sensors 2017, 2, 1860.

[10] H. Lee, C. Song, Y. S. Hong, M. S. Kim, H. R. Cho, T. Kang, K. Shin, S. H. Choi, T. Hyeon, D.-H. Kim, Sci Adv 2017, 3.

[11] Y.-T. Liao, H. Yao, A. Lingley, B. Parviz, B. P. Otis, IEEE Journal of Solid-State Circuits 2012, 47, 335.

[12] B. J. van Enter, E. von Hauff, Chem Commun (Camb) 2018, 54, 5032.
[13] H. Lee, Y. J. Hong, S. Baik, T. Hyeon, D. H. Kim, Adv Healthc Mater 2018, 7, e1701150.
[14] C. De Block, B. Manuel-y-Keenoy, L. Van Gaal, J Diabetes Sci Technol 2008, 2, 718.
[15] M. M. Rahman, A. J. Ahammad, J. H. Jin, S. J. Ahn, J. J. Lee, Sensors (Basel) 2010, 10, 4855.
[16] K. Tian, M. Prestgard, A. Tiwari, Mater Sci Eng C Mater Biol Appl 2014, 41, 100.
[17] K. E. Toghill, R. G. Compton, International Journal of Electrochemical Science 2010, 5, 1246.
[18] X. Y. Lang, H. Y. Fu, C. Hou, G. F. Han, P. Yang, Y. B. Liu, Q. Jiang, Nat Commun 2013, 4, 2169.
[19] Y. Ding, Y. Wang, L. Su, M. Bellagamba, H. Zhang, Y. Lei, Biosens Bioelectron 2010, 26, 542.
[20] H. Zhu, L. Li, W. Zhou, Z. Shao, X. Chen, Journal of Materials Chemistry B 2016, 4, 7333.
[21] S. R. Corrie, J. W. Coffey, J. Islam, K. A. Markey, M. A. Kendall, Analyst 2015, 140, 4350.
[22] X. Strakosas, J. Selberg, Z. Hemmatian, M. Rolandi, Adv Sci 2017, 4.
[23] C. Zhong, Y. Deng, A. F. Roudsari, A. Kapetanovic, M. P. Anantram, M. Rolandi, Nat Commun 2011, 2, 476.
[24] E. E. Josberger, P. Hassanzadeh, Y. X. Deng, J. Sohn, M. J. Rego, C. T. Amemiya, M. Rolandi, Sci Adv 2016, 2.
[25] Z. Hemmatian, S. Keene, E. Josberger, T. Miyake, C. Arboleda, J. Soto-Rodriguez, F. Baneyx, M. Rolandi, Nature Communications 2016, 7.
[26] J. Soto-Rodriguez, Z. Hemmatian, E. E. Josberger, M. Rolandi, F. Baneyx, Advanced Materials 2016, 28, 6581.
[27] T. Miyake, E. E. Josberger, S. Keene, Y. X. Deng, M. Rolandi, Apl Mater 2015, 3.
[28] Y. X. Deng, T. Miyake, S. Keene, E. E. Josberger, M. Rolandi, Sci Rep-Uk 2016, 6.
[29] Z. Hemmatian, E. Jalilian, S. Lee, X. Strakosas, A. Khademhosseini, A. Almutairi, S. R. Shin, M. Rolandi, Acs Appl Mater Inter 2018.
[30] S. Park, H. Boo, T. D. Chung, Anal Chim Acta 2006, 556, 46.
[31] P. Bollella, G. Fusco, C. Tortolini, G. Sanzo, G. Favero, L. Gorton, R. *Antiochia*, Biosens Bioelectron 2017, 89, 152.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-enzymatic sensing device, comprising:
   a non-enzymatic sensor;
   a power supply operatively connected to the non-enzymatic sensor; and
   at least one of:
   a signal processing and display system in communication with said sensor system to received sensor signals therefrom to be processed and results displayed, or
   a transmitter in communication with said sensor system to received sensor signals therefrom to be transmitted to an external device to be processed and results displayed, wherein the non-enzymatic sensor comprises:
   a substrate;
   a sensor contact disposed on the substrate; and
   a pH modifying contact disposed on the substrate proximate the sensor contact,
   wherein the pH modifying contact comprises a material that absorbs hydrogen ions from and expels hydrogen ions to a fluid when in use in response to applied voltages resulting in an electrically controllable change of pH of the fluid,
   wherein the pH modifying contact is positioned relative to the sensor contact such that the electrically controllable change of pH of the fluid results in a change in pH of the fluid proximal to the sensor contact to thereby enhanced detection of a substance of interest at the sensor contact without the use of enzymes.

2. The non-enzymatic sensing device according to claim 1, further comprising a reference contact arranged to be in contact with the fluid so as to be isolated from or sufficiently far from the pH modifying contact so that a pH of the fluid proximate the reference contact remains substantially unchanged by the pH modifying contact during operation.

3. The non-enzymatic sensing device according to claim 1, wherein said pH modifying contact comprises Pd formed on a layer of gold, and
   wherein the layer of gold is nanoporous in structure at least at an interface with the Pd.

4. The non-enzymatic sensing device according to claim 3, wherein said pH modifying contact comprises Pd nanoparticles having an ensemble average diameter of at least 60 nm and less than 240 nm.

5. The non-enzymatic sensing device according to claim 1, wherein the sensor contact comprises a catalyst for the detection of the substance of interest.

6. The non-enzymatic sensing device according to claim 5, wherein the catalyst comprises cobalt oxide and the substance of interest is glucose.

7. The non-enzymatic sensing device according to claim 1, further comprising a reference contact disposed on the substrate and in contact with the fluid so as to be isolated from or sufficiently far from the pH modifying contact so that a pH of the fluid proximate the reference contact remains substantially unchanged during operation by the pH modifying contact.

8. The non-enzymatic sensing device according to claim 7, wherein the reference contact has a surface area greater than a surface area of said pH modifying contact and greater than a surface area of said sensor contact.

9. The non-enzymatic sensing device according to claim 7, further comprising a membrane disposed on the pH modifying contact and the reference contact, the membrane preventing hydrogen ions from contacting the sensor contact after the pH in the fluid proximal to the sensor contact has been increased.

10. A non-enzymatic sensor, comprising:
    a substrate;
    a sensor contact disposed on the substrate; and
    a pH modifying contact disposed on the substrate proximate the sensor contact,
    wherein the pH modifying contact comprises a material that absorbs hydrogen ions from and expels hydrogen ions to a fluid when in use in response to applied voltages resulting in an electrically controllable change of pH of the fluid, wherein the pH modifying contact is positioned relative to the sensor contact such that the electrically controllable change of pH of the fluid results in a change in pH of the fluid proximal to the sensor contact to thereby enhanced detection of a substance of interest at the sensor contact without the use of enzymes.

11. The non-enzymatic sensor according to claim 10, wherein said pH modifying contact comprises Pd formed on a layer of gold, and
wherein the layer of gold is nanoporous in structure at least at an interface with the Pd.

12. The non-enzymatic sensor according to claim 11, wherein said pH modifying contact comprises Pd nanoparticles having an ensemble average diameter of at least 60 nm and less than 1 μm.

13. The non-enzymatic sensor according to claim 10, wherein the sensor contact comprises a catalyst for the detection of the substance of interest.

14. The non-enzymatic sensor according to claim 13, wherein the catalyst comprises cobalt oxide and the substance of interest is glucose.

15. The non-enzymatic sensor according to claim 10, further comprising a reference contact disposed on the substrate and in contact with the fluid so as to be isolated from or sufficiently far from the pH modifying contact so that a pH of the fluid proximate the reference contact remains substantially unchanged during operation by the pH modifying contact.

16. The non-enzymatic sensor according to claim 15, wherein the reference contact has a surface area greater than a surface area of said pH modifying contact and greater than a surface area of said sensor contact.

17. The non-enzymatic sensor according to claim 15, further comprising a membrane disposed on the pH modifying contact and the reference contact, the membrane preventing hydrogen ions from contacting the sensor contact after the pH in the fluid proximal to the sensor contact has been increased.

18. The non-enzymatic sensor according to claim 17, wherein the membrane comprises a hydrophilic proton conducting material that does not affect pH.

19. The non-enzymatic sensor according to claim 17, wherein the membrane comprises two layers of polymer layers in a stack configuration, a first layer at an interface with a sensing area, that is a hydrophilic polymer, and a second layer that is a charged polymer that will repel OH$^-$ from diffusing to the fluid.

20. A non-enzymatic method of detecting a substance of interest, comprising:
disposing a fluid containing the substance of interest on a sensing contact;
changing a pH of at least a portion of the fluid on the sensing contact by applying a voltage to a pH modifying contact that is also in contact with the fluid, the pH modifying contact comprising a material that absorbs hydrogen ions from and expels hydrogen ions to the fluid when in use in response to applied voltages resulting in an electrically controllable change of pH of the fluid; and
detecting the substance of interest using the sensing contact,
wherein the detecting is enhanced by the changing of the pH of the portion of the fluid on the sensing contact, and
wherein the detecting is a non-enzymatic method of detecting.

* * * * *